US008440189B2

(12) United States Patent
Rennert

(10) Patent No.: US 8,440,189 B2
(45) Date of Patent: *May 14, 2013

(54) ANTAGONISTS OF TWEAK AND OF TWEAK RECEPTOR AND THEIR USE TO TREAT IMMUNOLOGICAL DISORDERS

(75) Inventor: Paul Rennert, Millis, MA (US)

(73) Assignee: Biogen Idec MA Inc., Weston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/173,604

(22) Filed: Jun. 30, 2011

(65) Prior Publication Data

US 2012/0027751 A1 Feb. 2, 2012

Related U.S. Application Data

(63) Continuation of application No. 12/506,006, filed on Jul. 20, 2009, now abandoned, which is a continuation of application No. 11/542,745, filed on Oct. 4, 2006, now Pat. No. 7,579,001, which is a continuation of application No. 10/916,141, filed on Aug. 11, 2004, now Pat. No. 7,169,387, which is a continuation of application No. 09/905,810, filed as application No. PCT/US00/01044 on Jan. 14, 2000, now abandoned.

(60) Provisional application No. 60/116,168, filed on Jan. 15, 1999.

(51) Int. Cl.
*A61K 39/395* (2006.01)
(52) U.S. Cl.
USPC .............. 424/130.1; 424/133.1; 424/145.1
(58) Field of Classification Search .................. None
See application file for complete search history.

(56) References Cited

U.S. PATENT DOCUMENTS

| | | | |
|---|---|---|---|
| 4,921,698 | A | 5/1990 | Shirai et al. |
| 5,073,492 | A | 12/1991 | Chen et al. |
| 5,200,313 | A | 4/1993 | Carrico |
| 5,223,409 | A | 6/1993 | Ladner et al. |
| 5,225,539 | A | 7/1993 | Winter |
| 5,624,821 | A | 4/1997 | Winter et al. |
| 5,648,260 | A | 7/1997 | Winter et al. |
| 5,693,762 | A | 12/1997 | Queen et al. |
| 5,858,991 | A | 1/1999 | Hellerqvist et al. |
| 5,859,205 | A | 1/1999 | Adair et al. |
| 5,885,793 | A | 3/1999 | Griffiths et al. |
| 6,046,381 | A | 4/2000 | Mucke et al. |
| 6,207,642 | B1 | 3/2001 | Wiley |
| 6,300,064 | B1 | 10/2001 | Knappik et al. |
| 6,407,213 | B1 | 6/2002 | Carter et al. |
| 6,448,042 | B1 | 9/2002 | Greene et al. |
| 6,544,761 | B2 | 4/2003 | Greene et al. |
| 6,727,225 | B2 | 4/2004 | Wiley |
| 6,824,773 | B2 | 11/2004 | Wiley |
| 6,943,146 | B2 | 9/2005 | Jakubowski et al. |
| 7,087,725 | B2 | 8/2006 | Browning et al. |
| 7,109,298 | B2 | 9/2006 | Browning et al. |
| 7,129,061 | B1 | 10/2006 | Browning et al. |
| 7,169,387 | B2 | 1/2007 | Rennert |
| 7,208,151 | B2 | 4/2007 | Browning et al. |
| 7,482,430 | B2 | 1/2009 | Wiley |
| 7,495,086 | B2 | 2/2009 | Kim et al. |
| 7,507,807 | B2 | 3/2009 | Wiley |
| 7,517,962 | B2 | 4/2009 | Wiley |
| 7,566,769 | B2 | 7/2009 | Browning et al. |
| 7,579,001 | B2 | 8/2009 | Rennert |
| 7,695,934 | B2 | 4/2010 | Browning |
| 7,731,963 | B2 | 6/2010 | Browning et al. |
| 7,732,588 | B2 | 6/2010 | Wiley |
| 7,829,675 | B2 | 11/2010 | Kim et al. |
| 2002/0004041 | A1 | 1/2002 | Albert et al. |
| 2002/0015703 | A1 | 2/2002 | Rennert |
| 2002/0042368 | A1 | 4/2002 | Fanslow et al. |
| 2002/0110853 | A1 | 8/2002 | Wiley |
| 2003/0148314 | A1 | 8/2003 | Berger et al. |
| 2003/0162712 | A1 | 8/2003 | Cerretti et al. |
| 2003/0170228 | A1 | 9/2003 | Ashkenazi et al. |
| 2003/0198640 | A1 | 10/2003 | Yu et al. |
| 2003/0211096 | A1 | 11/2003 | Ashkenazi et al. |
| 2003/0211993 | A1 | 11/2003 | Jakubowski et al. |
| 2003/0216546 | A1 | 11/2003 | Tykocinski |
| 2004/0014176 | A1 | 1/2004 | Ashkenzai et al. |
| 2004/0018170 | A1 | 1/2004 | Shirwan |
| 2004/0033225 | A1 | 2/2004 | Browning et al. |
| 2004/0033495 | A1 | 2/2004 | Murray et al. |
| 2004/0038349 | A1 | 2/2004 | Hilbert et al. |
| 2004/0047854 | A1 | 3/2004 | Black et al. |
| 2004/0076955 | A1 | 4/2004 | Mack et al. |
| 2004/0091473 | A1 | 5/2004 | DuBose et al. |
| 2004/0175744 | A1 | 9/2004 | Hu et al. |
| 2004/0176296 | A1 | 9/2004 | Holtzman et al. |
| 2004/0203083 | A1 | 10/2004 | Buechler et al. |
| 2005/0008625 | A1 | 1/2005 | Balint et al. |
| 2005/0008636 | A1 | 1/2005 | Rennert |
| 2005/0079574 | A1 | 4/2005 | Bond |
| 2005/0112666 | A1 | 5/2005 | Browning et al. |
| 2005/0118629 | A1 | 6/2005 | Browning et al. |
| 2005/0181375 | A1 | 8/2005 | Aziz et al. |
| 2005/0208500 | A1 | 9/2005 | Erlander et al. |
| 2006/0003932 | A1 | 1/2006 | Jakubowski et al. |
| 2006/0240004 | A1 | 10/2006 | Burkly et al. |
| 2007/0110745 | A1 | 5/2007 | Rennert |
| 2007/0280940 | A1 | 12/2007 | Winkles et al. |

(Continued)

FOREIGN PATENT DOCUMENTS

| | | |
|---|---|---|
| CA | 2064710 A1 | 11/1991 |
| EP | 1 354 950 A1 | 10/2003 |

(Continued)

OTHER PUBLICATIONS

Sean Ricardo Campbell, The Role of TWEAK/Fn14 Interactions in Antibody Induced Glomerulonephritis. Dissertation, Nov. 2007.*

(Continued)

*Primary Examiner* — Maher Haddad
(74) *Attorney, Agent, or Firm* — Finnegan, Henderson, Farabow, Garrett & Dunner, LLP

(57) ABSTRACT

The present invention relates to reagents which modify the activity of TWEAK and their use as therapeutic agents for the treatment of immunological disorders.

13 Claims, 5 Drawing Sheets

U.S. PATENT DOCUMENTS

Figure 2B:
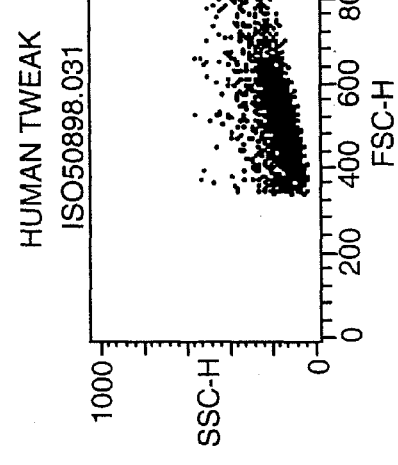
Figure 2D:
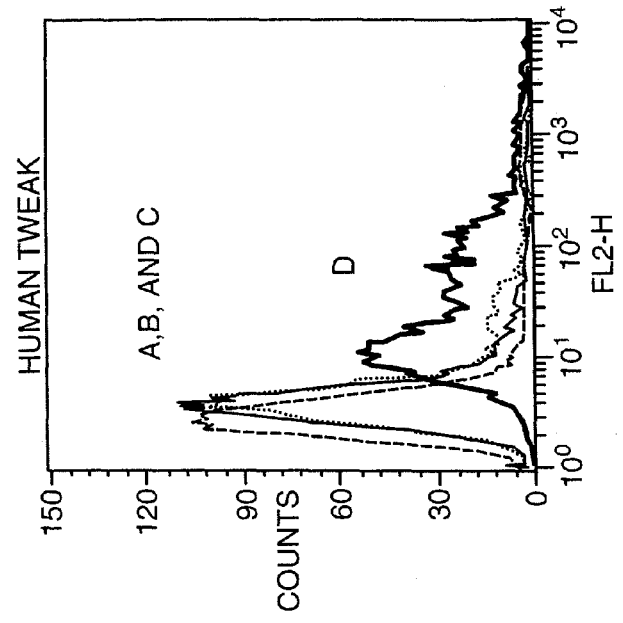
Figure 2A:
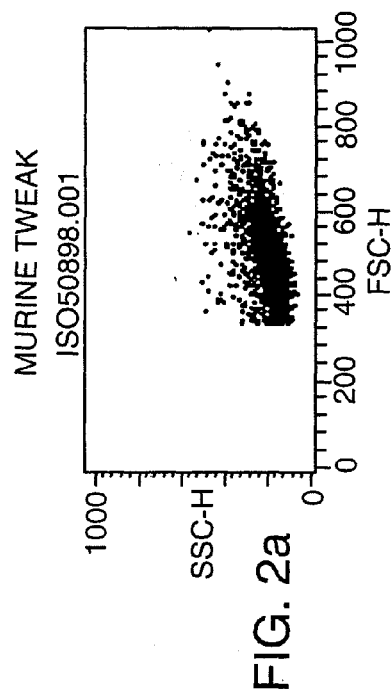
Figure 2C:
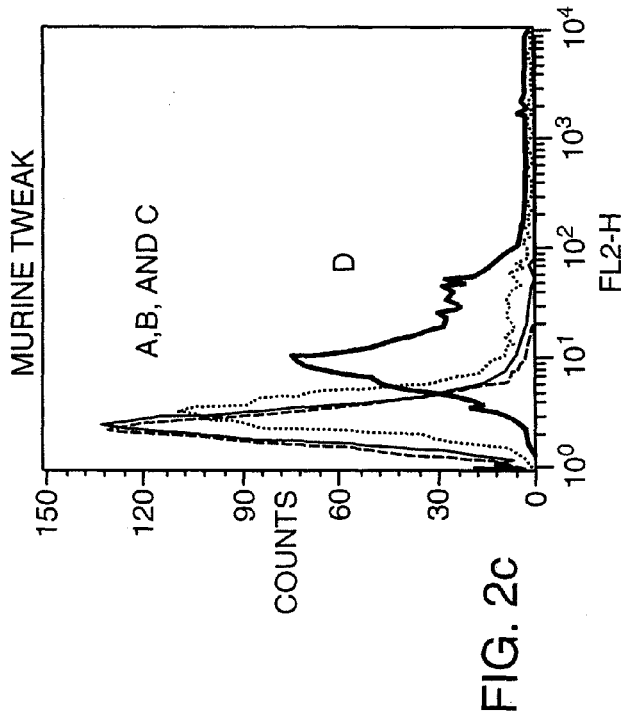

| | | | |
|---|---|---|---|
| 2008/0008714 A1 | 1/2008 | Browning et al. | |
| 2008/0187544 A1 | 8/2008 | Burkly et al. | |
| 2008/0241163 A1 | 10/2008 | Burkly et al. | |
| 2008/0279853 A1 | 11/2008 | Burkly et al. | |
| 2008/0286271 A1 | 11/2008 | Ashkenazi et al. | |
| 2008/0292622 A1* | 11/2008 | Burkly et al. | 424/133.1 |
| 2009/0068102 A1 | 3/2009 | Burkly et al. | |
| 2009/0124993 A1 | 5/2009 | Burkly et al. | |
| 2009/0311313 A1 | 12/2009 | Burkly et al. | |
| 2009/0324602 A1 | 12/2009 | Garber et al. | |
| 2010/0061985 A1 | 3/2010 | Rennert | |
| 2010/0183548 A1 | 7/2010 | Wiley | |
| 2010/0260761 A1 | 10/2010 | Browning et al. | |
| 2010/0272721 A1 | 10/2010 | Burkly et al. | |
| 2010/0284933 A1 | 11/2010 | Burkly | |
| 2011/0002924 A1 | 1/2011 | Browning et al. | |
| 2012/0009178 A1 | 1/2012 | Burkly et al. | |
| 2012/0014953 A1 | 1/2012 | Burkly et al. | |
| 2012/0015024 A1 | 1/2012 | Burkly et al. | |
| 2012/0020913 A1 | 1/2012 | Burkly | |
| 2012/0020970 A1* | 1/2012 | Burkly et al. | 424/135.1 |
| 2012/0121583 A1* | 5/2012 | Baehner et al. | 424/133.1 |
| 2012/0183542 A1 | 7/2012 | Burkly et al. | |

FOREIGN PATENT DOCUMENTS

| | | |
|---|---|---|
| EP | 1 566 636 A1 | 8/2005 |
| JP | 5-501062 A | 3/1993 |
| JP | 2002-527096 A | 8/2002 |
| WO | WO 95/14772 A1 | 6/1995 |
| WO | WO 96/18725 A1 | 6/1996 |
| WO | WO 98/05783 A1 | 2/1998 |
| WO | WO 98/35061 A2 | 8/1998 |
| WO | WO 98/52976 A1 | 11/1998 |
| WO | WO 98/55508 A2 | 12/1998 |
| WO | WO 99/11791 A2 | 3/1999 |
| WO | WO 99/19490 A1 | 4/1999 |
| WO | WO 99/59614 A1 | 11/1999 |
| WO | WO 99/61471 A2 | 12/1999 |
| WO | WO 00/23459 A1 | 4/2000 |
| WO | WO 00/34317 A2 | 6/2000 |
| WO | WO 00/37638 A2 | 6/2000 |
| WO | WO 01/45730 A2 | 6/2001 |
| WO | WO 01/53486 A1 | 7/2001 |
| WO | WO 01/85193 A2 | 11/2001 |
| WO | WO 02/22166 A2 | 3/2002 |
| WO | WO 02/102994 A2 | 12/2002 |
| WO | WO 03/040307 A2 | 5/2003 |
| WO | WO 03/086311 A2 | 10/2003 |
| WO | WO 2005/010045 | 2/2005 |
| WO | WO 2005/080972 A1 | 9/2005 |
| WO | WO 2006/047172 A1 | 5/2006 |
| WO | WO 2006/052926 A2 | 5/2006 |
| WO | WO 2006/088890 A2 | 8/2006 |
| WO | WO 2006/089095 A2 | 8/2006 |
| WO | WO 2006/096487 A2 | 9/2006 |
| WO | WO 2006/122187 A2 | 11/2006 |
| WO | WO 2006/130374 A2 | 12/2006 |
| WO | WO 2006/130429 A2 | 12/2006 |
| WO | WO 2006/138219 A2 | 12/2006 |
| WO | WO 2008/048924 A2 | 4/2008 |
| WO | WO 2009/140177 A2 | 11/2009 |
| WO | WO 2010/085648 A2 | 7/2010 |
| WO | WO 2010/088534 | 8/2010 |

OTHER PUBLICATIONS

Tschetter et al. Progression from acute to chronic disease in a murine parent-into-F1 model of graft-versus-host disease. J Immunol. Nov. 15, 2000;165(10):5987-94.*

Abbas, A.K. et al. (eds), "General Properties of Immune Responses", Introduction to Immunology, Cellular and Molecular Immunology. Philadelphia: WB Saunders Co., 1991; Chapter One, pp. 4-12.

Abbas, A.K. et al. (eds), "Immunity to Microbes", Cellular and Molecular Immunology. Philadelphia: WB Saunders Co., 1991; Chapter Fifteen, pp. 302-314.

Andrews et al., "Spontaneous murine Lupus-like Syndromes", J. Exp. Med. 148:1198-1215 (1978).

Ashkenazi et al., "Death Receptors: Signaling and Modulation", Science 281:1305-1308 (1998).

Bach-Elias et al., "Presence of autoantibodies against small nuclear ribonucleoprotein epitopes in Chagas' patients' sera", Parasitol. Res. 84:196-799 (1998).

Boucraut, J. et al., "Anti-TWEAK Monoclonal Antibodies Reduce CNS Immune Cell Infiltration and Severity of Experimental Autoimmune Encephalomyelitis" Meeting: Autoimmunity: Mechanisms and Novel Treatments, Mykonos, Greece, Oct. 8-13, 2003; Abstract No. 64.

Browning et al., "Characterization of Surface Lymphotoxin Forms", J. Immunol. 154:33-46 (1995).

Campbell, S. et al., "Proinflammtory Effects of TWEAK/Fn14 Interactions in Glomerular Mesangial Cells", J. Immunol. 176:1889-1898 (2006).

Campbell, S. et al., "The Role of Tweak/Fn14 in the Pathogenesis of Inflammation and Systemic Autoimmunity", Frontiers in Bioscience 9:2273-2284 (2004).

Cassiano, L. et al., "Molecular cloning of a novel receptor for TWEAK", Scand. J. Immunol. 51(Suppl. 1):1-111 (Abstract 2.2) (2000).

Chaplin et al., "Cytokine regulation of secondary lymphoid organ development", Curr. Opin. Immunol. 10:288-297 (1998).

Chicheportiche, Y. et al., "Down-Regulated Expression of TWEAK mRNA in Acute and Chronic Inflammatory Pathologies", Biochem. Biophys. Res. Commun. 279(1):162-165 (2000).

Chicheportiche, Y. et al., "Proinflammatory Activity of TWEAK on Human Dermal Fibroblasts and Synoviocytes; Blocking and Enhancing Effects of Anti-TWEAK Monoclonal Antibodies", Arthritis Res. 4(2):126-133 (2002). Epub Nov. 9, 2001.

Chicheportiche, Y. et al., "TWEAK, a new secreted ligand in the tumor necrosis factor family that weakly induces apoptosis", J. Biol. Chem. 272(51):32401-32410 (Dec. 19, 1997).

Courtenay et al., "Immunisation against heterologous type II collagen induces arthritis in mice", Nature 283:666-668 (1980).

Dallman, "Cytokines and transplantation: Th1/Th2 regulation of the immune response to solid organ transplants in the adult", Curr. Opin. Mmunol. 7:632-638 (1995).

De Wit et al., "Preferential Activation of Th2 Cells in Chronic Graft-versus-Host Reaction", J Immunol. 150(2):361-366 (1993).

Desplat-Jego, S. et al., "Anti-TWEAK monoclonal antibodies reduce immune cell infiltration in the central nervous system and severity of experimental autoimmune encephalomyelitis", Clin. Immunol. 117(1):15-23 (2005).

Desplat-Jego, S. et al., "TWEAK is Expressed by Glial Cells, Induces Astrocyte Proliferation and Increases EAE Severity", J. Neuroimmunol. 133:116-123 (2002).

Donahue, P.J. et al., "TWEAK is an Endothelial Cell Growth and Chemotactic Factor That Also Potentiates FGF-2 and VEGF-A Mitogenic Activity", Arterioscler. Thromb. Vasc. Biol. 23:594-600 (2003).

Durie et al., "Antibody to the Ligand of CD40, gp39, Blocks the Occurrence of the Acute and Chronic Forms of Graft-vs-Host Disease", J. Clin. Invest. 94:1333-1338 (1994).

Feng, S-L. Y., et al., "The Fn14 Immediate-Early Response Gene is Induced During Liver Regeneration and Highly Expressed in Both Human and Murine Hepatocellular Carcinomas", Am. J. Pathol. 156(4):1253-1261 (2000).

Flynn et al., "CD4 T Cell Cytokine Differentiation: The B Cell Activation Molecule, OX40 Ligand, Instructs CD4 T Cells to Express Interleukin 4 and Upregulates Expression of the Chemokine Receptor Bir-1", J. Exp. Med. 188:297-304 (1998).

Fujimoto et al., "Interleukin-6 Blockade Suppresses Autoimmune Arthritis in Mice by the Inhibition of Inflammatory Th17 Responses", Arthritis & Rheumatism 58:3710-3719 (2008).

Genentech, Inc., Full Prescribing Information for Actrema (Jan. 2010).

Gleichmann et al., "A systemic Lupus erythematosus (SLE)-like disease in mice induced by abnormal T-B cell cooperation", Eur. J. Immunol. 12:152-159 (1982).

Grewel et al., "The CD40 Ligand", Immunol. Res. 16:59-70 (1997).

Grewel et al., "The Role of CD40 Ligand in Costimulation and T-Cell Activation", Immunol. Rev. 153:85-106 (1996).

Hahm, K. et al., "TWEAK overexpression induces hyperplasia in liver and kidney", FASEB J. 17(4-5):Abstract No. 471.5 (2003).

Han, H. et al., "Identification of Differentially Expressed Genes in Pancreatic Cancer Cells Using cDNA Microarray", Cancer Research 62:2890-2896 (May 15, 2002).

Ho, D.H. et al., "Soluble Tumor Necrosis Factor-Like Weak Inducer of Apoptosis Overexpression in HEK293 Cells Promotes Tumor Growth and Angiogenesis in Athymic Nude Mice", Cancer Res. 64:8968-8972 (Dec. 15, 2004).

Jakubowski, A. et al., "Dual role for TWEAK in angiogenic regulation", J. Cell Sci. 115(Pt 2):267-274 (Jan. 15, 2002).

Jakubowski, A. et al., "TWEAK induces liver progenitor cell proiiferation", J. Clin. Invest. 115(9):2330-2340 (Sep. 2005).

Jakubowski, A. et al., "TWEAK Synergizes With Basis Fibroblast Growth Factor to Induce Endothelial Cell Proliferation, Migration and Lumen Morphogenesis", Scand. J. Immunol. 51(Suppl. 1):62, Abstract 1.30 (2000).

Kalled et al., "Anti-CD40 Ligand Antibody Treatment of SNF.sub.1 Mice with Established Nephritis: Preservation of Kidney Function", J. Immunol. 160:2158-2165 (1998).

Kamata et al., "Involvement of TNF-Like Weak Inducer of Apoptosis in the Pathogenesis of Collagaen-Induced Arthritis1" J. Immunol. 177:6433-6439 (2006).

Kaplan et al. "Th2 Lymphocytes Kill Antigen Presenting Macrophages Through a TWEAK Dependant Pathway", J. Invest. Med. 46:287A (1998).

Kawakita, T. et al., "Functional expression of TWEAK in human hepatocellular carcinoma: possible implication in cell proliferation and tumor angiogenesis", Biochem. Biophys. Res. Commun. 318:726-733 (2004).

Kirk et al., "CTLA4-Ig and anti-CD40 ligand prevent renal allograft rejection in primates", Proc. Natl. Acad. Sci. USA 94:8789-8794 (1997).

Kornek et al., "Multiple Sclerosis and Chronic Autoimmune Encephalomyelitis. A Comparative Quantitative Study of Axonal Injury in Active, Inactive, and Remyelinated Lesions". Am. J. Pathol. 157(1):267-276 (Jul. 2000).

Krenger et al., "Graft-versus-Host Disease and the Th1/Th2 Paradigm", Immunol. Res. 15:50-73 (1996).

Lenschow et al., "Differential Effects of Anti-B7-1 and Anti-B7-2 Monoclonal Antibody Treatment on the Development of Diabetes in the Nonobese Diabetic Mouse", J. Exp. Med. 181:1145-1155 (1995).

Lin et al., "Very late antigen 4 (VLA4) antagonists as anti-inflammatory agents", Curr. Opin. Chem. Biol. 2:453-457 (1998).

Lynch, C. et al., "TWEAK Induces Proliferation in Endothelial Cells and Substitutes for EGF and Hydrocortisone in Culture", J. Interferon Cytokine Res. 18:A-46, Abstract 2.16 (1998).

Lynch, C.N. et al., "TWEAK Induces Angiogenesis and Proliferation of Endothelial Cells", J. Biol. Chem. 274(13):8455-8459 (1999).

Mackay et al., "Turning off follicular dendritic cells", Nature 395:26-27 (1998).

Marsters et al., "Identification of a ligand for the death-domain-containing receptor Apo3", Current Biology 8:525-528 (1998).

Meighan-Mantha et al., "The Mitogen-inducible Fn14 Gene Encodes a Type I Transmembrane Protein that Modulates Fibroblast Adhesion and Migration", J. Biol. Chem. 274: 33166-33176 (Nov. 1999).

Michaelson, J.S. et al., "Tweak induces mammary epithelial branching morphogenesis", Oncogene 24:2613-2624 (2005).

Mohan et al., "Interaction Between CD40 and Its Ligand gp39 in the Development of Murine Lupus Nephritis", J. Immunol. 154.1470-1480 (1995).

Morris et al., "Experimental Induction of Systemic Lupus erythematosus by recognition of foreign Ia", Clin. Immunol. Immunopathol. 57:263-273 (1990).

Mueller, A.M. et al,, "Targeting fibroblast growth-factor-inducible-14 signaling protects from chronic relapsing experimental autoimmune encephalomyelitis", J. Neuroimmunol. 159(1-2):55-65 (2005).

Nagata, S., "Apoptosis by Death Factor" Cell 88:355-365 (1997).

Ngo et al., "Computational Complexity, Protein Structure Prediction, and the Levinthal Paradox", in The Protein Folding Problem. 1994; Chapter 14, pp. 435-508.

Perper, S.J. et al., "TWEAK is a novel arthritogenic mediator", J. Immunol. 177(4):2610-2620 (Aug. 15, 2006).

Potrovita, I. et al., "Tumor Necrosis Factor-Like Weak Inducer of Apoptosis-Induced Neurodegeneration", J. Neurosci. 24(38):8237-8244 (Sep. 22, 2004).

Potrovita, I. et al., "TWEAK—A Regulator of Neuronal Cell Death", Naunyn-Schmiedeberg's Archives of Pharmacology 369(Suppl. 1):R12 (Mar. 9, 2004).

Putterman, C. et al., "Tweak Blockade Improves Kidney Disease in Lupus-Prone Mice: A Novel Approach to the Treatment of Lupus Nephritis?", FASEB J., Experimental Biology 2004, Abstracts Part II, 18(5):Abstract No. 562.27 (2004).

Ruuls et al., "The Length of Treatment Determines Whether IFN-Beta Prevents or Aggravates Experimental Autoimmune Encephalomyelitis in Lewis Rats", J. Immunol. 157:5721-5731 (1993).

Saas, P. et al., "TWEAK Stimulation of Astrocytes and the Proinflammatory Consequences", GLIA 32(1):102-107 (2000).

Steinman, L. et al., "Virtues and pitfalls of EAE for the development of therapies for multiple sclerosis", Trends in Immunology 26(11);565-571 (2005).

Steinman, L., "Optic Neuritis, a New Variant of Experimental Encephalomyelitis, a Durable Model for All Seasons, Now in Its Seventieth Year", J. Exp. Med. 197(9):1065-1071 (2003).

Takagi et al, "Blockage of Interleukin-6 Receptor Ameliorates Joint Disease in Murine Collagen-Induced Arthritis", Arthritis & Rheumatism 41:2117-2121 (1998).

Techman, A., "Biogen Idec and University of Adelaide Find TWEAK is a Novel Arthritogenic Mediator; Potential New Pathway in Rheumatoid Arthritis and Osteoarthritis Disease Process" Aug. 16, 2006, pp. 1-2.

Theien, B.E. et al., "Discordant effects of anti-VLA-4 treatment before and after onset of relapsing experimental autoimmune encephalomyelitis", J. Clin. Invest. 107:995-1006 (2001).

Tibbetts et al., "Cardiac Antigen-Specific Autoantibody Production is Associated with Cardiomyopathy in Typansoma cruzi-Infected Mice.sup.1", J. Immunol., vol. 152, pp. 1493-1499 (1994).

Toogood et al., "The Immune Response Following Small Bowel Transplantation", Transplantation 62(6):851-855 (1996).

Tran, N.L. et al., "The Human Fn14 Receptor Gene is Up-Regulated in Migrating Glioma Cells in Vitro and Overexpressed in Advanced Glial Tumors", Am. J. Pathol. 162(4):1313-1321 (Apr. 2003).

Tran, N.L. et al., "The Tumor Necrosis Factor-like Weak Inducer of Apoptosis (TWEAK)-Fibroblast Growth Factor-inducible 14 (Fn14) Signaling System Regulates Glioma Cell Survival via NFkappaB Pathway Activation and BCL-XL/BCL-W Expression", J. Biol. Chem. 280(5):3483-3492 (Feb. 4, 2005).

Trauth et al., "Monoclonal Antibody-Mediated Tumor Regression by Induction of Apoptosis", Science 245:301-305 (1989).

Trentham et al., "Autoimmunity to Type II Collagen: An Experimental Model of Arthritis", J. Exp. Med. 146:857-868 (1977).

Uchiyama et al., "Tocilizomab, a Humanized Anti-interleukin-6 Receptor Antibody, Ameliorates Joint Swelling in Established Monkey Collagen-Induced Arthritis", Biol. Pharm Bull. 31(6):1159-1163 (2008).

U.S. Appl. No. 09/169,104, filed Oct. 9, 1998, Ashkenazi et al.

Ward et al., "Blocking of adhesion molecules in vivo as anti-inflammatory therapy", Ther. Immunol. 1(3):165-171 (1994).

Wiley et al., "Identification and Characterization of a New Member of the TNF Family That Induces Apoptosis", Immunity 3:673-682 (1995).

Wiley, S.R. et al., "A Novel TNF Receptor Family Member Binds TWEAK and is implicated in Angiogenesis", Immunity 15:837-846 (2001).

Wiley, S.R. et al., "TWEAK, a member of the TNF superfamily, is a multifunctional cytokine that binds the TweakR/Fn14 receptor", Cytokine & Growth Factor Reviews 14:241-249 (2003).

Williamson et al., "IL-12 is a Central Mediator of Acute Graft-Versus-Host Disease in Mice", J. Immunol. 157(2):689-699 (1996).

Winkles, J.A. et al., "Role of TWEAK and Fn14 in tumor biology", Frontiers in Bioscience 12:2761-2771 (Jan. 1, 2007).

Zhao, Z. et al., "TWEAK/Fn14 Interactions are Instrumental in the Pathogenesis of Nephritis in the Chronic Graft-versus-Host Model of Systemic Lupus Erythematosis", J. Immunol. 179:7949-7958 (2007).

Abreu-Martin et al., "Divergent Induction of Apoptosis and IL-8 Secretion in HT-29 Cells in Response to TNF-α and Ligation of Fas Antigen", *J. Immunol.* 155:4147-4154 (1995).

Agrawal, "Antisense Oligonucleotides: Towards Clinical Trials", *TIBTECH* 14:376-387 (1996).

Akahori et al., "Immunoglobulin kappa light chain VLJ region [*Homo sapiens*]", NCBI database accession No. GI:21669075, GenBank Accession No. BAC01562 (Jun. 25, 2001).

Amakawa et al., "Impaired Negative Selection of T Cells in Hodgkin's Disease Antigen CD30-Deficient Mice", *Cell* 84:551-562 (1996).

Anderson, "Human Gene Therapy", *Nature* 392:25-30 (1998).

Angal et al., "A single amino acid substitution abolishes the heterogeneity of chimeric mouse/human (IgG4) antibody", *Mol. Immunol.* 30:105-108 (1993).

Badley et al., "Upregulation of Fas Ligand Expression by Human Immunodeficiency Virus in Human Macrophages Mediates Apoptosis of Uninfected T Lymphocytes", *J. Virology* 70:199-206 (1996).

Barrios et al., "Length of the antibody heavy chain complementarity determining region 3 as a specificity-determining factor", *J. Mol. Recog.* 17:332-338 (2004).

Bateller et al., "Liver fibrosis", *J. Clin. Invest.*, 115(2):209-218 (2005).

Bendele et al., "Combination Benefit of Treatment with the Cytokine Inhibitors Interleukin-1 Receptor Antagonist and PEGylated Soluble Tumor Necrosis Factor Receptor Type 1 in Animal Models of Rheumatoid Arthritis", *Arthritis Rheum.* 43(12):2648-2659 (2000).

Bodmer et al., "TRAMP, a Novel Apoptosis-Mediating Receptor with Sequence Homology to Tumor Necrosis Factor Receptor 1 and Fas(Apo-1/CD95)", *Immunity* 6:79-88 (1997).

Boor et al., "Treatment targets in renal fibrosis", *Nephrol. Dial. Transplant.* 22:3391-3407 (2007).

Bose et al., "Problems in using statistical analysis of replacement and silent mutations in antibody genes for determining antigen-driven affinity selection", *Immunology* 116:172-183 (2005).

Bowie et al., "Deciphering the Message in Protein Sequences: Tolerance to Amino Acid Substitutions", *Science* 247:1306-1310 (1990).

Branch, "A good antisense molecule is hard to find", *TIBS* 23:45-50 (1998).

Brojatsch et al., "CAR1, a TNFR-Related Protein, Is a Cellular Receptor for Cytopathic Avian Leukosis-Sarcoma Viruses and Mediates Apoptosis", *Cell* 87:845-855 (1996).

Browning et al., "Preparation and Characterization of Soluble Recombinant Heterotrimeric Complexes of Human Lymphotoxins Alpha and Beta", *J. Biol. Chem.* 271:8618-8626 (1996).

Browning et al., "Signaling through the Lymphotoxin Beta Receptor Induces the Death of Some Adenocarcinoma Tumor Lines", *J. Exp. Med.* 183:867-878 (1996).

Browning et al., "Studies on the Differing Effects of Tumor Necrosis Factor and Lymphotoxin on the Growth of Several Human Tumor Lines", *J. Immunol.* 143:1859-1867 (1989).

Browning, J., Second Declaration under 37 CFR 1.132 of Jeffrey Browning, Ph.D. from U.S. Appl. No. 09/245,198, Declaration filed on Jun. 27, 2005.

Bucher et al., "A Generalized Profile Syntax for Biomolecular Sequence Motifs and Its Function in Automatic Sequence Interpretation", Proc. Second International Conference on Intelligent Systems for Molecular Biology. Altman, Brutlag, Karp, Lathrop, Searls (Eds.), pp. 53-61 (1994).

Castro et al., "Fas Modulation of Apoptosis during Negative Selection of Thymocytes" *Immunity* 6:617-627 (1996).

Chothia et al., "Structural repertoire of the human $V_H$ segments", *J. Mol. Biol.* 227:799-817 (1992).

Clackson et al., "Making antibody fragments using phage display libraries" *Nature* 352:624-628 (1991).

Clark et al., "Trends in antibody sequence changes during the somatic hypermutation process", *J. Immunol.* 177:333-340 (2006).

Cwirla et al., "Peptides on Phage: A Vast Library of Peptides for Identifying Ligands", *Proc. Natl. Acad. Sci. USA* 87:6378-6382 (1990).

Darnay et al., "Signal Transduction by Tumor Necrosis Factor and Tumor Necrosis Related Ligands and Their Receptors", *Ann. Rheum. Dis.* 58(Suppl. 1):I2-I13 (1999).

David et al., "A study of the structural correlates of affinity maturation: Antibody affinity as a funcetion of chemical interactions, structural plasticity and stability", *Molecular Immunology* 44:1342-1351 (2007).

Davies et al., "Single antibody domains as small recognition units: design and in vitro antigen selection of camelized, human VH domains with improved protein stability", *Protein Eng.* 9(6):531-537 (1996).

De Benedette et al., "Role of 4-1BB Ligand in Costimulation of T Lymphocyte Growth and its Upregulation on M12 B Lymphomas by cAMP", *J. Exp. Med.* 181:985-992 (1995).

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody" *J. Immunol.* 169:3076-3084 (2002).

Degli-Esposti, "To die or not to die—the quest of the TRAIL receptors", *J. Leukocyte Biol.* 65:535-542 (1999).

Dermer, "Another Anniversary for the War on Cancer", *BioTechnology* 12:320 (1994).

Dias et al., "The Role of CXC Chemokines in the Regulation of Tumor Angiogenesis", *Cancer Invest.* 19:732-738 (2001).

Droz, D., "Clinico-anatomical forms of primary glomerulonephritis", *Rev. Med. Interne* 15(6):390-398 (1994) (Abstract only; article in French).

Eck et al., "The Structure of Human Lymphotoxin (Tumor Necrosis Factor-Beta) at 1.9-Å Resolution", *J. Biol. Chem.* 267:2119-2122 (1992).

European Patent Application No. 03721647: Supplementary Partial Search Report, dated Aug. 9, 2005.

European Patent Application No. 06760258: Extended Search Report, including Search Opinion and Supplementary Search Report, dated Jun. 19, 2009.

European Patent Application No. 08104327: Extended Search Report, including Search Opinion, dated Feb. 6, 2009.

European Patent Application No. 10181803: Extended Search Report, including Search Opinion, dated Jul. 6, 2012.

European Patent Application No. 10181810: Extended Search Report, including Search Opinion, dated Jul. 6, 2012.

Falk et al., "Expression of the APO-1 Antigen in Burkitt Lymphoma Cell Lines Correlates with a Shift Towards a Lymphoblastoid Phenotype", *Blood* 79:3300-3306 (1992).

Fox, D., "Biological Therapies: A Novel Approach to the Treatment of Autoimmune Disease", *Am. J. Med.* 99:82-88 (1995).

Funakoshi et al., "Inhibition of Human B-Cell Lymphoma Growth by CD40 Stimulation", *Blood* 83:2787-2794 (1994).

Galle et al., "Involvement of the CD95 (APO-1/Fas) Receptor and Ligand in Liver Damage" *J. Exp. Med.* 182:1223-1230 (1995).

Gauchat et al., "Human CD40-Ligand: Molecular Cloning, Cellular Distribution and Regulation of Expression by Factors Controlling IgE Production", *FEBS Lett.* 315:259-266 (1993).

Genbank Acc. No. AAB49141, "Anti-DNA immunoglobulin heavy chain IgG [*Mus musculus*]" (1996).

Gruss et al., "Pleiotrophic Effects of the CD30 Ligand on CD30-Expressing Cells and Lymphoma Cell Lines", *Blood* 83:2045-2056 (1994).

Gruss et al., "Tumor Necrosis Factor Ligand Superfamily: Involvement in the Pathology of Malignant Lymphomas" *Blood* 85:3378-3404 (1995).

Han et al., "Overexpression of FN14/TEAK receptor in pancreatic cancer", *Proc. Am. Assoc. Cancer Res. Annual Meeting* 46(Suppl. S):Abstract No. 2363 (Apr. 18, 2005).

Hess et al., "A Novel Function of CD40: Induction of Cell Death in Transformed Cells", *J. Exp. Med.* 183:159-167 (1996).

Hillier, L. et al., "The Wash U-Merck EST project yy19a08.s1 *Homo sapiens* cDNA clone 2716703", EMBL Database Entry HS070272, Accesion No. N35070 (Jan. 19, 1996).

Hillier, L. et al., "The WashU-Merck EST project yy19a08.s1 *Homo sapiens* cDNA clone 1547425", EMBL Database Entry HS379117, Accession No. R55379 (May 28, 1995).

Ike et al., "Solid Phase Synthesis of Polynucleotides. VIII. Synthesis of Mixed Oligodeoxyribonucleotides by the Phosphotriester Solid Phase Method", *Nucl. Acids Res.* 11:477-488 (1983).

International Search Report issued in International Patent Application No. PCT/US03/11350; Date of Mailing: Mar. 10, 2004.

International Search Report and Written Opinion issued in International Patent Application No. PCT/US06/022830; Date of Mailing: Jan. 26, 2007.

International Search Report and Written Opinion issued in International Patent Application No. PCT/US06/19706; Date of Mailing: Oct. 9, 2007.

Jain et al., "A Novel Role for Tumor Necrosis Factor Like Weak Inducer of Apoptosis (TWEAK) in the Development of Cardiac Dysfunction and Failure", *Circulation* 119:2058-2068, with supplemental material (2009).

Juengst, "What next for human gene therapy", *BMJ* 326:1410-1411 (2003).

Kaduka et al., "TWEAK Mediates Anti-Tumor Effect of Tumor-Infiltrating Macrophage", *Biochem. Biophys. Res. Commun.* 331:384-390 (2005).

Kaplan et al., "The Apoptotic Ligands TRAIL, TWEAK, and Fas Ligand Mediate Monocyte Death Induced by Autologous Lupus T Cells", *J. Immunol.* 169:6020-6029 (2002).

Kaplan et al., "TRAIL (Apo2 Ligand) and TWEAK (Apo3 Ligand) Mediate CD4$^+$ T Cell Killing of Antigen-Presenting Macrophages", *J. Immunol.* 164:2897-2904 (2000).

Katsikis et al., "Fas Antigen Stimulation Induces Marked Apoptosis of T Lymphocytes in Human Immunodeficiency Virus-infected Individuals", *J. Exp. Med.* 181:2029-2036 (1995).

Kobrin et al., "A V region mutation in a phosphocholine-binding monoclonal antibody results in loss of antigen binding", *J. Immunol.* 146:2017-2020 (1991).

Lee et al., "T Cell Receptor-dependent Cell Death of T Cell Hybridomas Mediated by the CD30 Cytoplasmic Domain in Association with Tumor Necrosis Factor Receptor-Associated Factors", *J. Exp. Med.* 183:669-674 (1996).

Lennon et al., "The I.M.A.G.E. Consortium: An Integrated Molecular Analysis of Genomes and Their Expression", *Genomics* 33:151-152 (Apr. 1996) with Medline Abstract page.

Lund et al., "Human FcγRI and FcγRII interact with distinct but overlapping sites on human IgG", *J. Immunol.* 147:2657-2662 (1991).

Markan et al., "Up regulation of the GRP-78 and GADD-153 and down regulation of Bcl-2 proteins in primary glomerular diseases: a possible involvement of the ER stress pathway in glomerulonephritis", *Mol. Cell Biochem.* 324:131-138 (2009).

Marra et al., "The WashU-HHMI Mouse EST project. my18d09.r1 Barstead mouse heart MPLRB3 *Mus musculus* cDNA clone 696209 5'" GenBank Database Accession No. AA221610 (Feb. 15, 1997).

Martin-Villalba et al., "Therapeutic Neutralization of CD-95-Ligand and TNF Attenuates Brain Damage in Stroke", *Cell Death Diff.* 8:679-686 (2001).

Miller et al., "Genetic Studies of the *lac* Repressor. IX. Generation of Altered Proteins by the Suppression of Nonsense Mutations", *J. Mol. Biol.* 131:191-222 (1979).

Montgomery et al., "Herpes Simplex Virus-1 Entry into Cells Mediated by a Novel Member of the TNF/NGF Receptor Family", *Cell* 87:427-436 (1996).

Morgan et al., "The N-terminal end of the $C_H2$ domain of chimeric human IgG1 anti-HLA-DR is necessary for C1q, FcγRI and FcγRIII binding", *Immunology* 86:319-324 (1995).

Murphy, "Revisiting graft-versus-host disease models of autoimmunity: new insights in immune regulatory processes", *J. Clin. Invest.* 106(6):745-747 (2000).

Nakaya et al., "Regulation of Asialoglycoprotein Receptor Synthesis by Inflammation-Related Cytokines in HepG2 Cells", *J. Gastroenterol.* 29:24-30 (1994).

Nakayama et al., "Characterization of murine TWEAK and its receptor (Fn14) by monoclonal antibodies", *Biochem. Biophys. Res. Commun.* 306(4):819-825 (2003).

Nakayama et al., "Fibroblast Growth Factor-Inducible 14 Mediates Multiple Pathways of TWEAK-Induced Cell Death", *J. Immunol.* 170:341-348 (2003).

Nakayama et al., "Involvement of TWEAK in Interferon γ-stimulated Monocyte Cytotoxicicity", *J. Exp. Med.* 192(9):1373-1379 (2000).

Neutra et al., "Intestinal Epithelium: A Model System for Study of Cell Differentiation and Polarized Cell Functions", in *Functional Epithelia Cells in Culture*. Liss (ed.), 1989; pp. 363-398.

Ngo et al., In *The Protein Folding Problem and Tertiary Structure Prediction*. K. Merz Jr. and S. Legrand (Eds.) Birkhauser, Boston, 1994; pp. 433 and 492-495.

Orkin et al., Report and Recommendations of the Panel to Assess the NIH Investment in Research on Gene Therapy (Dec. 7, 1995).

Patent Interference No. 105,513, Paper 106, Memorandum Opinion and Order, Decision on Motions.

Patent Interference No. 105,513, Paper 107, Decision—Bd. R. 125, Decision on Browning Misc. Motion 4 for Sanctions.

Patent Interference No. 105,513, Paper 108, Judgement, Preliminary Motions—Bd. R. 127.

Paul, "Fv Structure and Diversity in Three Dimensions", in *Fundamental Immunology*, 3rd. edition. New York: Raven Press, 1993; pp. 292-295.

Pepper et al., "Biphasic effect of transforming growth factor-β1 on in vitro angiogenesis", *Exp. Cell Res.* 204(2):356-363 (Feb. 1993).

Pitti et al., "Induction of Apoptosis by Apo-2 Ligand, a New Member of the Tumor Necrosis Factor Cytokine Family", *J. Biol. Chem.* 271:12687-12690 (1996).

Plowman et al., "Human Tumor Xenograft Models in NCI Drug Development", in *Anticancer Drug Development Guide: Preclinical Screening Clinical Trials and Approval*. B. Teicher (ed.), Humana Press Inc., Totown, 1997; pp. 101-125.

Portanova et al., "Lupus-like autoimmunity in murine graft-versus-host disease", *Concepts Immunopathol.* 6:119-140 (1988).

Portolano et al., "Lack of promiscuity in autoantigen-specific H and L chain combinations as revealed by human H and L chain 'Roulette'" *J. Immunol.* 150(3):880-887 (1993).

Roberts et al., "Directed Evolution of a Protein: Selection of a Potent Neutrophil Elastase Inhibitors Displayed on M13 Fusion Phage", *Proc. Natl. Acad. Sci. USA* 89:2429-2433 (1992).

Romano et al., "Latest developments in gene transfer technology: achievements, perspectives, and controversies over therapeutic applications", *Stem Cells* 18:19-39 (2000).

Rosenberg et al., "Gene therapist, heal thyself", *Science* 287:1751 (2000).

Rovin et al., "Urine chemokines as biomarkers of human systemic lupus erythematosus activity", *J. Am. Soc. Nephrol.* 16:467-473 (2005).

Rudikoff et al., "Single amino acid substitution altering antigen-binding specificity", *Proc. Natl. Acad. Sci. USA* 79(6):1979-1983 (1982).

Rudinger, "Characteristics of the amino acids as components of a peptide hormone sequence", in *Peptide Hormones*. J.A. Parsons (Ed.), University Park Press, Baltimore, MD, 1976; pp. 1 and 6.

Rus et al., "Kinetics of Th1 and Th2 Cytokine Production During the Early Course of Acute and Chronic Murine Graft-Versus-Host Disease", *J. Immunol.* 155:2396-2406 (1995).

Saemann et al., "Urinary tract infection in renal transplant recipients" *Eur. J. Clin. Invest.* 38(Suppl. 2):58-65 (2008).

Scamurra et al., "Ig heavy chain variable region VH3 family [*Homo sapiens*]", NCBI database Accession No. GI:33318898, GenBank Accession No. AAQ05352 (2002).

Schneider et al., "TWEAK Can Induce Cell Death via Endogenous TNF and TNF Receptor 1", *Eur. J. Immunol.* 29(6):1785-1792 (1999).

Semov et al., "Alterations in TNF- and IL-related Gene Expression in Space-flown WI38 Human Fibroblasts", *FASEB J.* 16(8):899-901 (2002).

Shepard et al., "Monoclonal Antibody Therapy of Human Cancer: Taking the HER2 Protooncogene to the Clinic", *J. Clin. Immunol.* 11:117-127 (1991).

Smith et al., "CD30 Antigen, a Marker for Hodgkin's Lymphoma, Is a Receptor Whose Ligand Defines an Emerging Family of Cytokines with Homology to TNF", *Cell* 73:1349-1360 (1993).

Somia et al., "Gene therapy: trials and tribulations", *Nature Reviews Genetics* 1:91-99 (2000).

Song et al., "A single amino acid change (Asp 53→Ala53) converts Survivin from anti-apoptotic to pro-apoptotic", *Mol. Biol. Cell* 15:1287-1296 (Mar. 2004).

Stryer et al., in *Biochemistry*, 3rd Ed., W.H. Freeman and Co.: New York, 1988; pp. 31-33.

Stuber et al., "The T Cell-B Cell Interaction via OX40-OX40L is Necessary for the T Cell-dependent Humoral Immune Response", *J. Exp. Med.* 183:979-989 (1996).

Sytwu et al., "The Roles of Fas/APO-1 (CD95) and TNF in Antigen-Induced Programmed Cell Death in T Cell Receptor Transgenic Mice", *Immunity* 5:17-30 (1996).

Tannenbaum et al., "The CXC Chemokines IP-10 and Mig are Necessary for IL-12-Mediated Regression of the Mouse RENCA Tumor", *J. Immunol.* 161:927-932 (1998).

Tartaglia et al., "The Two Different Receptors for Tumor Necrosis Factor Mediate Distinct Cellular Responses", *Proc. Natl. Acad. Sci. USA* 88:9292-9296 (1991).

Tomlinson et al., "The repertoire of human germline $Vh_H$ sequences reveals about fifty groups of $V_H$ segments with different hypervariable loops", *J. Mol. Biol.* 227:776-798 (1992).

Tomlinson et al., "The structural repertoire of the human Vk domain" *EMBO J.* 14:4628-4638 (1995).

Verma et al., "Gene therapy—promises, problems and prospect", *Nature* 18:239-242 (1997).

Via "Advances in lupus stemming from the parent-into-F1 model", *Trends Immunol.* 31:236-245 (2010).

Via et al., "Role of cytotoxic T lymphocytes in the prevention of lupus-like disease occurring in a murine model of graft-vs-host disease", *J. Immunol.* 139:1840-1849 (1987).

Wada et al., "Detection of urinary interleukin-8 in glomerular diseases" *Kidney International* 46:455-460 (1994).

*Webster's II New Riverside University Dictionary*, "Preventing", Boston, Mass.: Houghton Mifflin Co., 1994; p. 933.

Winkles et al., "TWEAK and Fn14: New molecular targets for cancer therapy?", *Cancer Letters* 235:11-17 (2006).

Wuthrich et al., "Autoimmune tubulointerstitial nephritis: insight from experimental models", *Exp. Nephrol.* 6(4):288-293 (1998).

Yonehara et al., "A Cell-Killing Monoclonal Antibody (ANTI-Fas) to a Cell Surface Antigen Co-Downregulated with the Receptor of Tumor Necrosis Factor", *J. Exp. Med.* 169:1747-1756 (1989).

Zhao et al., "Different Gene Expression Patterns in Invasive Lobular and Ductal Carcinomas of the Breast", *Mol. Biol. Cell* 15:2523-2536 (Jun. 2004).

Zhu et al., "Inhibition of tumor growth and metastasis by targeting tumor-associated angiogenesis with antagonists to the receptors of vascular endothelial growth factor", *Investigational New Drugs* 17:195-212 (1999).

\* cited by examiner

| | | |
|---|---|---|
| Human | 1 | MAARRSQRRRGRRGEPGTALLVPLALGLGLALACLGLLLAVVSLGSRASL |
| Mouse | 1 | ------------------------VLSLGLALACLGLLLVVVSLGSWATL |
| Human | 51 | SAQEPAQEELVAEEDQDPSELNPQTEESQDPAPFLNRLVRPRRSAPKGRK |
| Mouse | 27 | SAQEPSQEELTAEDRREPPELNPQTEESQDVVPFLEQLVRPRRSAPKGRK |
| Human | 101 | TRARRAIAAHYEVEHPRPGQDGAQAGVDGTVSGWEEARINSSSPLRYNRQI |
| Mouse | 77 | ARPRRAIAAHYEVEHPRPGQDGAQAGVDGTVSGWEETKINSSSPLRYDRQI |
| Human | 151 | GEFIVTRAGLYYLYCQVHFDEGKAVYLKLDLLVDGVLALRCLEEFSATAA |
| Mouse | 127 | GEFTVIRAGLYYLYCQVHFDEGKAVYLKLDLLVNGVLALRCLEEFSATAA |
| Human | 201 | SSLGPQLRLCQVSGLLALRPGSSLRIRTLPWAHLKAAPFLTYFGLFQVH |
| Mouse | 177 | SSPGPQLRLCQVSGLLPLRPGSSLRIRTLPWAHLKAAPFLTYFGLFQVH |

FIG. 1

SEQUENCE LISTING

```
<160> NUMBER OF SEQ ID NOS: 2

<210> SEQ ID NO 1
<211> LENGTH: 225
<212> TYPE: PRT
<213> ORGANISM: Mus musculus

<400> SEQUENCE: 1

Val Leu Ser Leu Gly Leu Ala Leu Ala Cys Leu Gly Leu Leu Leu Val
1               5                   10                  15

Val Val Ser Leu Gly Ser Trp Ala Thr Leu Ser Ala Gln Glu Pro Ser
            20                  25                  30

Gln Glu Glu Leu Thr Ala Glu Asp Arg Arg Glu Pro Pro Glu Leu Asn
        35                  40                  45

Pro Gln Thr Glu Glu Ser Gln Asp Val Val Pro Phe Leu Glu Gln Leu
    50                  55                  60

Val Arg Pro Arg Arg Ser Ala Pro Lys Gly Arg Lys Ala Arg Pro Arg
65                  70                  75                  80

Arg Ala Ile Ala Ala His Tyr Glu Val His Pro Arg Pro Gly Gln Asp
                85                  90                  95

Gly Ala Gln Ala Gly Val Asp Gly Thr Val Ser Gly Trp Glu Glu Thr
            100                 105                 110

Lys Ile Asn Ser Ser Ser Pro Leu Arg Tyr Asp Arg Gln Ile Gly Glu
        115                 120                 125

Phe Thr Val Ile Arg Ala Gly Leu Tyr Tyr Leu Tyr Cys Gln Val His
    130                 135                 140

Phe Asp Glu Gly Lys Ala Val Tyr Leu Lys Leu Asp Leu Leu Val Asn
145                 150                 155                 160

Gly Val Leu Ala Leu Arg Cys Leu Glu Glu Phe Ser Ala Thr Ala Ala
                165                 170                 175

Ser Ser Pro Gly Pro Gln Leu Arg Leu Cys Gln Val Ser Gly Leu Leu
            180                 185                 190

Pro Leu Arg Pro Gly Ser Ser Leu Arg Ile Arg Thr Leu Pro Trp Ala
        195                 200                 205

His Leu Lys Ala Ala Pro Phe Leu Thr Tyr Phe Gly Leu Phe Gln Val
```

-continued

```
            210                 215                 220
His
225

<210> SEQ ID NO 2
<211> LENGTH: 249
<212> TYPE: PRT
<213> ORGANISM: Homo sapiens

<400> SEQUENCE: 2

Met Ala Ala Arg Arg Ser Gln Arg Arg Gly Arg Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
                180                 185                 190

Glu Glu Phe Ser Ala Thr Ala Ala Ser Ser Leu Gly Pro Gln Leu Arg
            195                 200                 205

Leu Cys Gln Val Ser Gly Leu Leu Ala Leu Arg Pro Gly Ser Ser Leu
        210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245
```

ANTAGONISTS OF TWEAK AND OF TWEAK RECEPTOR AND THEIR USE TO TREAT IMMUNOLOGICAL DISORDERS

CROSS-REFERENCE TO RELATED APPLICATIONS

This application is a continuation of U.S. application Ser. No. 12/506,006, filed Jul. 20, 2009, now abandoned, which is a continuation of U.S. application Ser. No. 11/542,745, filed Oct. 4, 2006, now U.S. Pat. No. 7,579,001 issued Aug. 25, 2009, which is a continuation of U.S. application Ser. No. 10/916,141, filed on Aug. 11, 2004, now U.S. Pat. No. 7,169,387 issued Jan. 30, 2007, which is a continuation of U.S. application Ser. No. 09/905,810, filed Jul. 13, 2001, now abandoned, which is the U.S. national phase of International Application no. PCT/US00/01044, filed on Jan. 14, 2000 (published as WO 00/42073 on Jul. 20, 2000), which claims benefit of provisional Application No. 60/116,168, filed Jan. 15, 1999. The disclosures of each of these prior applications are incorporated by reference in their entireties in the disclosure of this application.

FIELD OF THE INVENTION

The present invention relates to compositions and methods comprising reagents which bind to the novel protein TWEAK, and the use of TWEAK binding reagents to block the development of immunologic disorders. TWEAK binding reagents include monoclonal antibodies, as used herein to block the development of chronic Graft-Versus-Host Disease, soluble TWEAK-receptor-Ig fusion proteins, or other molecules which modify the binding of TWEAK to its' receptor(s). Other embodiments of the invention include reagents which bind to TWEAK receptor(s) to modify their activity, or modify the intracellular signaling of TWEAK receptor(s).

BACKGROUND OF THE INVENTION

Immunological disorders are manifested as a wide variety of diseases and pathologies, including autoimmune diseases, acute and chronic inflammatory disorders, organ transplant rejection, Graft-Versus-Host Disease (GVHD), lymphoid cell malignancies, septic and other forms of shock, loss of immune responsiveness as seen in HIV and SCIDS, and failure of the immune response to tumor growth.

Many immunological disorders are triggered by aberrant or uncontrolled responses to antigen. Autoimmune diseases are the result of the inappropriate response of the immune system to self-antigens, resulting in damage to cells and tissues. GVHD develops when donor cells from a bone marrow transplant (BMT) respond to host (i.e. patient) antigens. Organ transplant rejection results when the patient's immune system responds to antigens derived from the transplanted organ. Acute inflammatory disorders such as hyper-allergic conditions and shock are the result of uncontrolled immune response to the triggering antigens.

T cell dependent immune responses require T cell recognition of antigen. For example, GVHD results from a complex interplay between donor T cells and host immune system cells. The initiating event is the recognition by donor T cells of non-self, i.e. host, antigens. These are referred to as alloantigens. Alloantigen recognition by these donor cells results in the production of immunoregulatory and inflammatory cytokines and chemokines, which advance and exacerbate the donor anti-host immune response. This disease can develop in either an acute or chronic form, depending on the regulation of complex cytokine networks which control the type of immune response which develops. Immune responses can be characterized as Th0, Th1, or Th2 depending on 1) the nature of the cytokines and chemokines produced by activated T cells during the response, and 2) the nature of the cytokines and chemokines produced by accessory and other cells during the response. Examples of non-T cells important during immune responses are B cells, dendritic cells, monocytes and macrophages, follicular dendritic cells, and endothelial cells. Together the cytokines produced influence a variety of cell types to differentiate, and the chemokines produced influence cell trafficking and localization. Th0 responses are characteristic of the short term stimulation of previously unstimulated (naive) T cells. Th0 T cells produce moderate amounts of a number of cytokines, notably Il-2 and TNF. Repetitively or chronically stimulated Th0 cells can differentiate into either Th1 or Th2 T cells, depending on a number of factors. Such factors include, but are not limited to, accessory cell cytokine production, the strength of T cell receptor engagement, and the nature of secondary signals received, e.g. via the CD28 costimulatory receptor. In particular exposure of activated T cells to the cytokine Il-12, produced primarily by activated macrophages, supports differentiation to Th1 T cells, while exposure to Il-4 and Il-10 supports differentiation to Th2 T cells.

Th1 T cells produce cytokines such as Il-2 and IFN-γ which are associated with inflammatory responses, T cell cytotoxicity, and macrophage activation. Th1 T cells respond to chemokines which attract cells into sites of tissue inflammation, such as Mip-1alpha, MIP-1beta, RANTES, IP-10, and MIG. Since cytotoxic T cells and activated macrophages act to eliminate damaged or infected cells, the Th1 response is responsible for controlling the immune response to intracellular pathogens. Importantly, production of Th1 chemoattractant chemokines such as IP-10 and MIG by macrophages and endothelial cells is closely regulated by IFN-γ, which is the prototypic chemokine produced by Th1 T cells. Thus feedback loops may develop between activated T cells and their environment, which augment the development of a particular type of response at a particular time and location.

Th2 T cells produce cytokines such as Il-4, Il-5, Il-6, and Il-10 which support the development of humoral immune responses, including those which require the production of IgE, IgA, and IgG. These Ig responses are driven by the T cell mediated activation of B cells which "switch" their Ig phenotype from surface bound IgM and IgD to secreted Ig. Secreted Igs normally function to control infection from pathogens in circulation (IgG), at mucosal surfaces, such as the gut and oral cavity (IgA) and in the respiratory tract (IgE). Overproduction of Ig can cause disease, for example in SLE (IgG and IgA), allergic (Type I) hypersensitivity (IgE), and GVHD (IgG, IgA, and IgE). Th2 T cells also support the activation of eosinophils and Mast cells which can mediate acute responses to pathogens, for example in the respiratory tract. Th2 T cells respond to chemokines such as eotaxin and MDC, whose production is closely regulated by Il-4, the prototypic cytokine produced by NK1.1 and activated T cells.

The interaction of T cells with B cells is a complex and closely regulated process. To begin the activation process, B cells must receive an antigen signal through the B cell antigen receptor (membrane Ig). Secondly, B cells must receive specific contact dependent and contact independent signals from activated T cells. One required contact dependent signal is delivered via the binding of CD40L on T cells to CD40 on B cells. One required contact-independent signal is delivered by Il-4 secreted by activated T cells and by NK1.1 cells binding to the Il-4 receptor on B cells. These signals appear to take place within the T cell areas of secondary lymphoid organs, such as the spleen. The spleen, lymph nodes, tonsils, Peyer's patches and other secondary and tertiary lymphoid organs have distinct microanatomical areas within which T and B cells typically reside. All lymphocytes migrate out of the blood or the lymph into the T cell area of these organs first, by crossing endothelial cell layers such as the High Endothelial Venules in lymph nodes and Peyer's patches and the marginal sinus endothelial cell layer in the spleen. Then, the B cells move into B cell areas known as B cell follicles, B cells which have traversed the T cell area but have not become activated will leave the follicle after a few days. Activated B cell undergo a process of differentiation. Some activated B cells, known as plasmacytes, secrete large amounts of antigen specific, low affinity IgM or IgG antibody. These B cells typically appear early after the induction of the immune response, and move into the red pulp of the spleen and other anatomical locations, where they persist, secreting antibody, for several days. Other activated B cells differentiate within a region of the follicle known as the secondary follicle, or germinal center. Germinal centers form around networks of specialized antigen retaining cells known as Follicular Dendritic Cells (FDC), which are thought to display antigen to drive or refine the germinal center reaction. B cells within the germinal center have "switched" their Ig phenotype, and undergo "affinity maturation", with the result that they display a high affinity for their antigen target. Normally, the antigen target is a foreign antigen, although in diseases such as chronic GVHD and autoimmune disorders the Igs recognize self-antigens. Finally, B cells leave the follicles, migrate back through the T cells areas, and leave the organ via efferent circulation into the bloodstream.

B cells that have fully differentiated to express high affinity Ig are known as blast cells, and they leave B cell follicles to take up residence in various other environments, including the red-pulp areas of the spleen, the bone marrow, the liver, or mucosal cell layers lining the respiratory tract and gut. Some of these fully differentiated B cells are known as memory cells, and can persist for long periods of time, ready to respond to the same antigen if it is encountered again.

As B cells migrate from location to location within the lymphoid organs they require specific signals to guide them, and specific signals which ensure their survival. For example, multiple signals are required to maintain B cell follicular organization in the spleen. These include interaction of the BOA ligand with the chemokine receptor BLR-1, interaction of TNF with TNF-R55, and interaction of LTbeta with LTβ-R (reviewed in Chaplin and Fu, Current Opin. Immunol. 10: 298-297 (1998)). Mice which are deficient in any of these molecular pathways lose B cell follicular integrity in the spleen. Furthermore, all of these gene-deficient mice have also lost the ability to undergo germinal center reactions in the spleen. Disruption of other molecular pathways affects the germinal center reaction only. For example, mice deficient in CD40L maintain B cell follicles, but germinal centers do not form. B cells within the germinal center environment require signals through 0040 to maintain survival and to downregulate IgM and switch to Ig expression.

B cells move not only within the follicle and germinal center, but also leave the follicle after activation, and move to other sites within the body. Memory B cells can be found in the bone marrow, and B cells which express IgA specifically traffic to cell layers in the gut and other mucosal sites. Other signals presumably guide activated T cells to specific sites within and between lymphoid compartments. For example, cytotoxic T cell can migrate to the site of infection or other antigen challenge to find and lyse their targets. The identities of all the signals which guide T and B cells between different microanatomic locations are not yet known. However it appears that multiple pathways orchestrate the T and B cell responses to antigen, both in secondary lymphoid organs, and at the sites of infection or inflammation.

GVHD is a well studied example of an antigen driven immune response. GVHD is an often fatal consequence of bone marrow transplantation (BMT) in human patients. The disease can occur in an acute or in a chronic form. Acute and chronic forms of GVHD are prototypic examples of the development of antigen specific Th1 and Th2 responses, respectively. The acute form of the disease occurs within the first 2 months following BMT, and is characterized by donor cytotoxic T cell-mediated damage to skin, gut, liver, and other organs. The chronic form of the disease is manifested much later (over 100 days post-BMT) and is characterized by hyperproduction of immunoglobulin (Ig), including autoantibodies, and damage to the skin, kidney, and other organs caused by Ig-deposition. The development of acute GVHD is predictive of the subsequent development of chronic GVHD. Thus, the same patient can develop both diseases, in sequence. Approximately 50% of all BMT patients develop either acute or chronic GVHD. Nearly 90% of acute GVHD patients go on to develop chronic GVHD. No current therapies for chronic GVHD are successful in the majority of patients.

GVHD can be modeled in the mouse using parental into F1 cell transplantation regimens. In the model described here, splenocytes from the DBA2 strain of mice are injected iv into (DBA2×C57BI/6) F1 mice, which are referred to as B6D2F1. The injected splenocytes constitute the graft, and the DBA2 mouse is the donor of that graft. The F1 mouse which receives the graft is the host, Donor T cells present in the graft recognize half of the MHC markers (haplotypes) on host cells as foreign, because they are derived from the other, C57BI/6 parent, This induces a donor T cell response against the host resulting in GVHD. When DBN2 parental splenocytes are injected into the B6D2F1 host, chronic GVHD develops. In contrast when C57BI/6 splenocytes are injected into the B6D2F1 host, acute GVHD develops. Although it remains unclear what underlying mechanism is responsible for the distinct disease outcomes using these 2 injection protocols it is believed that the cytokines expressed by the cells contained within the DBA/2 splenocyte graft favor the development of chronic GVHD while the cytokines expressed by the cells contained within the C57BI/6 splenocyte graft favor the development of acute GVHD. Reagents which interfere with T cell interactions with antigen presenting cells (e.g. dendritic cells, macrophages, B cells: APC) effectively block both acute and chronic GVHD.

A number of lines of evidence suggest that acute GVHD is a Th1 mediated disease (Krenger and Ferrara, Immunol. Res. 15: 50-73 (1996), Williamson et al., J. Immunol, 157: 689-699 (1996)). Cytotoxic activity by CD4+ and CD8+ T cells, by natural killer (NK) cells, and by activated granulocytes such as macrophages, is a well defined consequence of Th1 mediated T cell response, and shows a characteristic dependence on the expression of Il-2 and IFN-γ, which are typical Th1 cytokines. Such cytotoxicity is a defining characteristic of acute GVHD. Furthermore, reagents which block critical cytokines involved in Th1 T cell differentiation, such as mAbs to Il-2 and Il-12, block the development of acute GVHD. Cytotoxicity can be directly cellular (e.g. by phagocytosis of host cells) or by the action of secreted cytokines such as TNF which can induce apoptosis, or cell death. The consequence of donor anti-host cytotoxicity can be seen in a number of ways. First, host lymphocytes are rapidly destroyed, such that mice experiencing acute GVHD are profoundly immunosuppressed. Secondly, donor lymphocytes become engrafted and expand in the host spleen, and their cytotoxic activity can be directly measured in vitro by taking advantage of cell lines which express the host antigens that can be recognized (as foreign) by the donor cells. For example, cell lines expressing the appropriate antigens can be labeled with radioactive chromium51 isotope. Release of this radioactive isotope into the culture media is evidence of the death of the labeled cell. Third, the disease becomes lethal as additional tissues and cell populations are destroyed, and therefore survivorship is a measurable consequence of disease.

Chronic GVHD appears to be a Th2 T cell mediated disease (De Wit et al., J. Immunol. 150: 361-366 (1993)). In the mouse model the development of the disease is dependent on the Th2 cytokine 114, and can be blocked by treating with anti-114 mAb. Such treatment blocks the expansion of host B cells, and the concomitant hyper-Ig production. The development of GVHD can be followed in a number of ways. The expansion of the donor T cell and host B cell populations can be measured by the spleen index, which is the ratio of spleen weight to body weight, normalized to control (non-diseased) mice. The activation of B cells in diseased mice can be measured using analyses of B cell activation markers. Finally, the effects of B cell activation can be seen in the levels of Ig in circulation (eg. in serum) or produced by cultures of host splenocytes harvested several weeks after disease induction. Circulating Ig in diseased animals will contain anti-self antibodies. Ultimately, diseased animals succumb to kidney and other organ failure due to accumulated Ig deposition, and therefore survivorship is a relevant measure of disease activity.

We now show that a monoclonal antibody specific for TWEAK effectively and specifically blocks aspects of the development of GVHD, using the mouse model of chronic GVHD. The block in development of chronic GVHD is shown as a reduction in the spleen index, the loss of activation markers on host B cells, and reduced Ig production in the anti-TWEAK treated animals.

SUMMARY OF THE INVENTION

The invention provides methods for blocking the development or treating or reducing the severity or effects of an immunological disorder in an animal including administering a pharmaceutical composition which comprises a therapeutically effective amount of a TWEAK blocking agent and a pharmaceutically acceptable carrier. The compound may be an antibody directed against a TWEAK ligand; an antibody directed against a TWEAK receptor; an agent that modifies the binding of the TWEAK ligand to a TWEAK receptor; an agent that modifies cell surface receptor clustering; and an agent that can interrupt intracellular signaling of a TWEAK receptor. In a preferred embodiment the antibody is a monoclonal antibody. In a more preferred embodiment the monoclonal antibody is directed against the TWEAK surface ligand. The animal may be mammalian and may be a human. The TWEAK blocking agent may be a soluble TWEAK receptor having a ligand binding domain that can selectively bind to a surface TWEAK ligand. In one embodiment the soluble TWEAK receptor may include a human immunoglobulin IgG domain. In a preferred embodiment, the human immunoglobulin IgG domain includes regions responsible for specific antigen binding.

The invention further includes a method for inhibiting an immune response in an animal, including administering a pharmaceutical composition which comprises an effective amount of a TWEAK blocking agent and a pharmaceutically effective carrier. The immune response may be Th1 or a Th2 cell-mediated immune response or both.

The invention also includes a composition having a therapeutically effective amount of a TWEAK blocking agent and a pharmaceutically acceptable carrier.

BRIEF DESCRIPTIONS OF THE DRAWINGS

FIG. 1 shows a sequence alignment of soluble recombinant murine (SEQ ID NO:1) and human (SEQ ID NO:2) TWEAK proteins. Identical residues are indicated in bold face.

FIG. 2 shows a Fluorescent Activated Cell Sorting (FACS) analysis of the binding of hamster anti-TWEAK mAb AB.D3 to EBNA293 cells expressing murine TWEAK protein or human TWEAK protein, compared to the binding of a hamster mAb which recognizes an irrelevant protein (Keyhole Limpet Hemocyanin). 2a) Analysis of anti-TWEAK mAb binding to murine TWEAK transfected EBNA293 cells (forward scatter (size) and side scatter (granularity)); 2b) analysis of anti-TWEAK mAb binding to human TWEAK transfected EBNA293 cells (forward scatter (size) and side scatter (granularity)); 2c) histogram showing PE-reactivity of anti-TWEAK mAb binding to murine TWEAK transfected EBNA293 cells: A. unstained cells, B. stained with streptavidin-PE, C. stained with control mAb Ha4/8, biotinylated goat anti-hampster IgG, and steptavidin-PE, D. stained with AB.D3, biotinylated goat anti-hamster IgG, and steptavidin-PE; 2d) histogram showing PE-reactivity of anti-TWEAK mAb binding to human TWEAK transfected EBNA293 cells: A. unstained cells, B. stained with streptavidin-PE, C. stained with control mAb Ha4/8, biotinylated goat anti-hampster IgG, and steptavidin-PE, D. stained with AB.D3, biotinylated goat anti-hamster IgG, and steptavidin-PE.

Figure 3B:
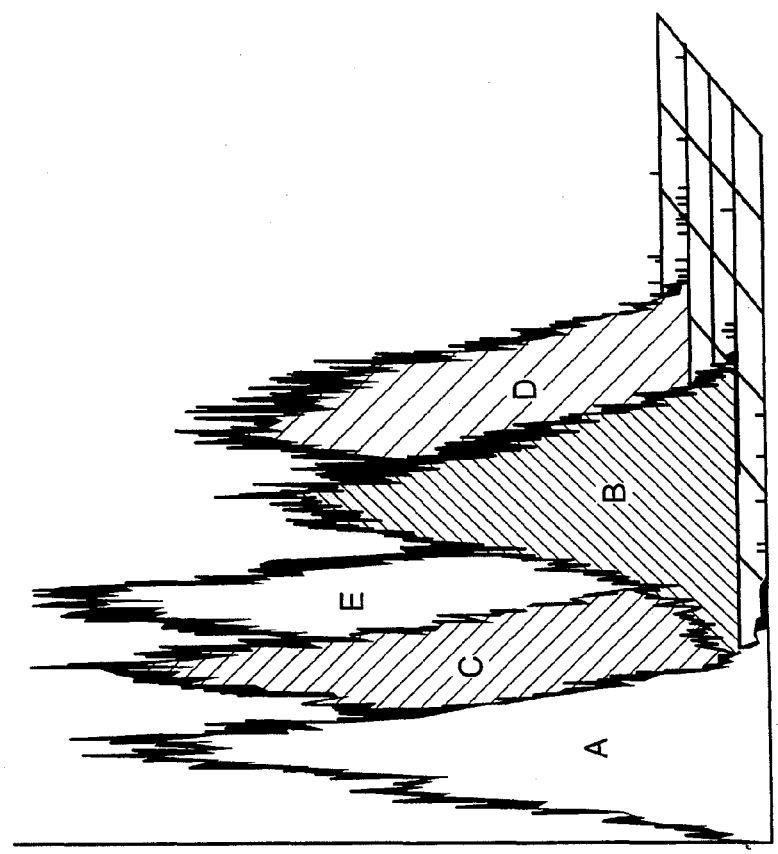
Figure 3A:
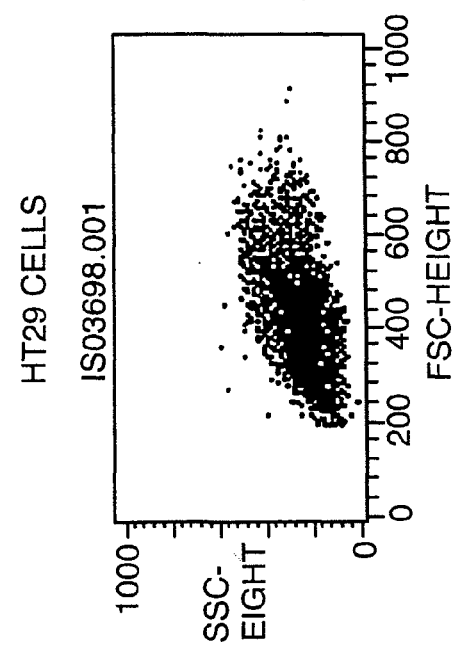
Figure 4B:
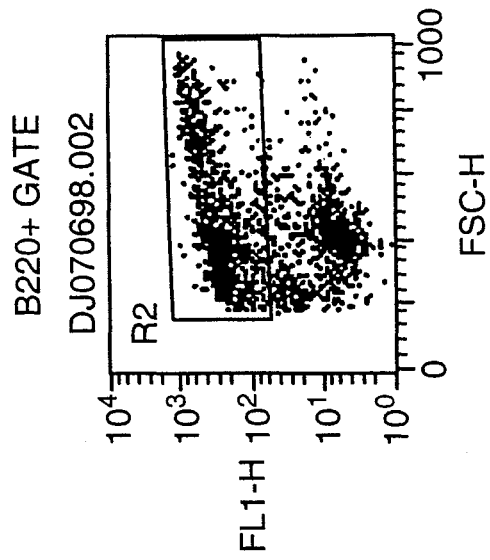
Figure 4A:
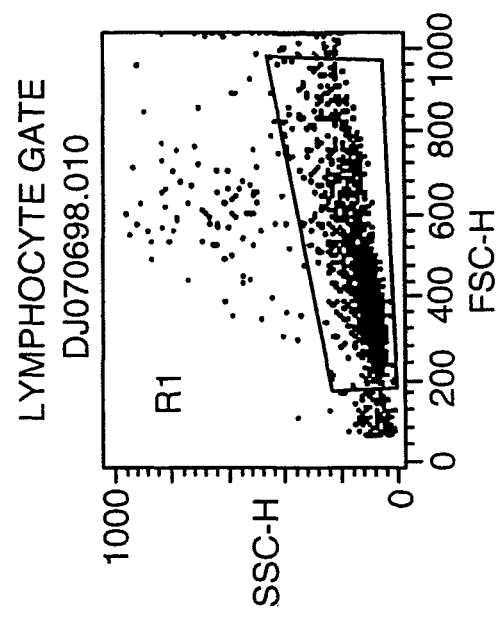
Figure 4C:
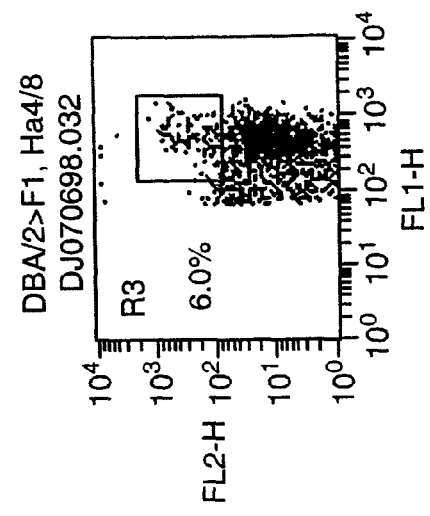
Figure 4D:
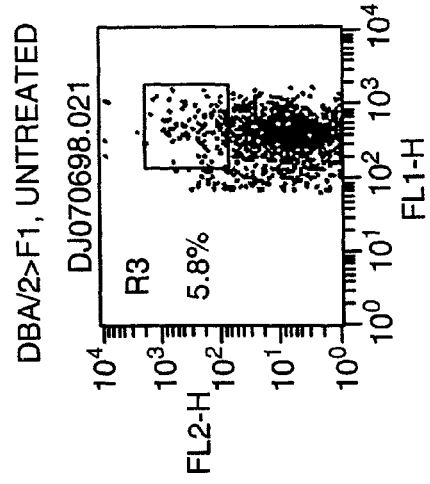
Figure 4E:
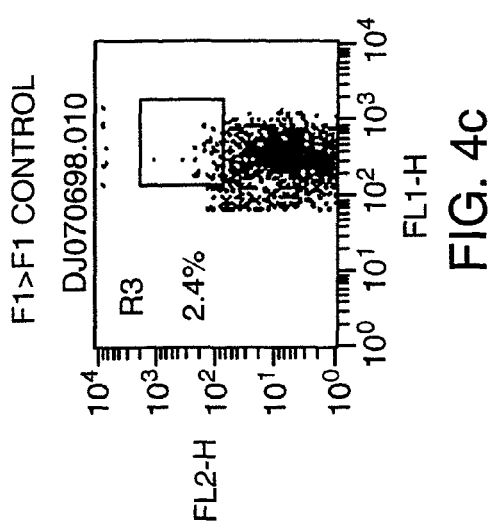
Figure 4F:
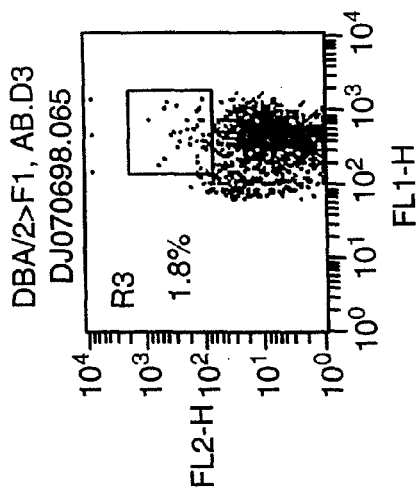
Figure 4G:
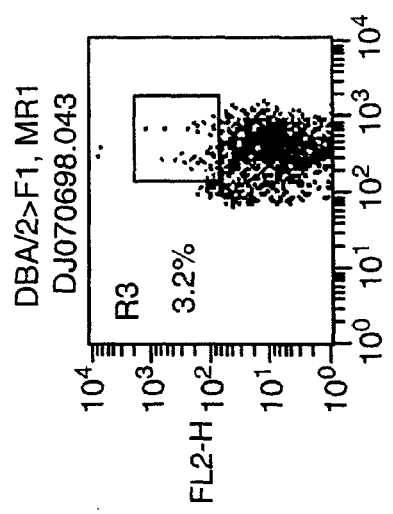

FIG. 3 shows a FACS analysis of the ability of mAb AB.D3 to block the binding of FLAG-tagged recombinant soluble human TWEAK to TWEAK receptor positive cells. 3a) HT29 cell population showing forward scatter and side scatter; 3b) HT29 cells incubated A. alone, or with 1 ug Flag-tagged human TWEAK protein plus B. no mAB, C. bug mAb AB.D3, D. 10 bug control hamster mAb, or E. 10 ug soluble murine TWEAK.

FIG. 4 shows a FACS analysis of the activation state of B cells in mice undergoing chronic GVHD, treated with anti-TWEAK mAb AB.D3, anti-CD40L mAb MR1, control mAb, or untreated. 4a) Derivation of the lymphocyte gate used in the analysis; 4b) derivation of the B220+ gate used in the analysis; 4c-g) splenocytes derived from mice with chronic GVHD, treated as labeled, and gated using R1 and R2. FL1 shows FITC-anti B220 staining and FL2 shows PE-antiCD69 staining. R3 encompasses the B220+/CD69+ cells.

DETAILED DESCRIPTION OF THE INVENTION

Definitions

In order that the invention herein described may be fully understood, the following detailed description is set forth.

The terms "humoral response" and "cellular response" as used herein refer to the immunological response of an animal to an antigen whereby the animal produces antibodies to an antigen or produces a cytotoxic response to the antigen, or both. The Th1 class of T helper cells are important for the induction of the cellular response, and the Th2 class of T helper cells are important to the efficient production of high affinity antibodies.

The term "T helper (Th) cells" as used herein, refers to a functional subclass of T cells which help to generate cytotoxic T cells and which cooperate with B cells to stimulate antibody production. Helper T cells recognize antigen in association with class II MHC molecules and provide contact dependent and contact independent (cytokine and chemokine) signals to effector cells.

The term "Th1" refers to a subclass of T helper cells that produce TNF, interferon-γ and IL-2 (and other cytokines) and which elicit inflammatory reactions associated with a cellular, i.e. non-immunoglobulin, response to a challenge.

The term "Th2" refers to a subclass of T helper cells that produces IL-4, IL-5, IL-6, IL-10, and other cytokines, which are associated with an immunoglobulin (humoral) response to an immune challenge.

The term "germinal center" as used herein refers to a secondary B cell follicle which forms after antigen immunization. The appearance of this histologic site correlates with optimal memory generation, isotype switching, somatic hypermutation and thus the affinity maturation of an antibody response.

The term "antibody producing cells" refers to B cells which have received contact dependent and contact independent signals from Th cells, and are secreting immunoglobulins of the IgM, IgG, IgA, or IgE subclasses.

The term "Fc domain" of an antibody refers to a part of the molecule comprising the hinge, CH2 and CH3 domains, but lacking the antigen binding sites. The term is also meant to include the equivalent regions of an IgM or other antibody isotype.

The term "anti-TWEAK antibody" refers to any antibody that specifically binds to at least one epitope of the TWEAK protein.

The term "anti-TWEAK receptor antibody" refers to any antibody that specifically binds to at least one epitope of a TWEAK receptor.

The term "TWEAK receptor signaling" refers to molecular reactions associated with a TWEAK receptor pathway and subsequent molecular reactions which result therefrom.

The terms "TWEAK or TWEAK-receptor modifying agent" and "TWEAK or TWEAK-receptor modifying reagent" refers to any agent that can modify ligand binding to a TWEAK receptor, can modify cell surface TWEAK receptor clustering or TWEAK receptor signaling, or that can influence how a TWEAK receptor signal is interpreted within the cell.

The term "TWEAK ligand" or "TWEAK protein" refers to any TWEAK monomeric, polymeric, or heteromeric complex or derivative thereof that can specifically bind to a TWEAK receptor.

The term "subject" refers to an animal, or to one or more cells derived from an animal. Preferably, the animal is a mammal. Cells may be in any form, including but not limited to cells retained in tissue, cell clusters, immortalized, transfected or transformed cells, and cells derived from an animal that has been physically or phenotypically altered.

TWEAK Ligand

TWEAK is a recently discovered member of the TNF family of proteins (Chicheportiche et al., J. Biol. Chem. 272: 32401-32410 (1997)). Members of the TNF family of proteins bind to receptors of the TNF-receptor (TNF-R) family of proteins. The interaction of proteins of the TNF family with their receptors influence a wide variety of functions within the immune system. Well known examples include the CD40L protein, which binds to the CD40 receptor to promote the differentiation of B cells into antibody producing cells (Grewal and Flavell, Immunol, Res. 16: 59-70 (1997)), the lymphotoxin-beta ligand (LT-β), which binds to the lymphotoxin-beta receptor to influence humoral immune responses by regulating the differentiation state of follicular dendritic cells (Mackay and Browning, Nature 395: 26-27 (1998)), and the OX40L, which binds the OX40 receptor to regulate the response of B cells to T cell signals (Flynn et al., J. Exp. Med. 188: 297-304 (1998)). Other ligand/receptor pairs within the TNF/TNF-R families which are known to play critical roles in the immune system include TNF/TNF-R55, FasL/Fas, and CD27/CD70.

TWEAK biology is as yet only partly understood. Purified soluble TWEAK protein was used to induce the differentiation and/or death of some tumor cell lines, including HT29 adenocarcinoma cells (cell death via apoptosis), HeLa cervical carcinoma cells (morphological changes), and A375 melanoma cells (anti-proliferation). TWEAK also induced the HT29 and A375 cell lines to secrete the chemokine IL-8, and had the same effect on a fibroblast cell line, WI-38 (Chicheportiche et al., J. Biol. Chem. 51: 32401-32410 (1997)). In addition TWEAK induced proliferation of a variety of normal endothelial cell lines (Lynch et al., J. Interferon Cytokine Res. 18: A-46 (1998)).

A putative receptor for TWEAK has been described (Marsters et al., Curr. Biol. 8: 525-528 (1998)) 1998). This receptor, variably known as TRAMP, Apo3, WSL-1, DR-3, or LARD is a member of the TNF-R family. Activation of TRAMP can induce apoptosis by engaging either the caspase-dependant cell death signaling pathway or cellular activation via NF-kB signaling pathways (Ashkenazi and Dixit, Science 281: 1305-1308 (1998)).

The expression of TWEAK in mouse and human tissues is widespread, with messenger RNA (mRNA) found in heart, brain, lung, liver, among other tissues, and secondary lymphoid organs such as spleen, lymph nodes, and peripheral blood mononuclear cells (PBMCs). TWEAK does not appear to be expressed in the primary lymphoid organs where immune system cells develop, such as thymus, bone marrow, and fetal liver. Thus the roles that TWEAK may play in the immune system are likely be in immune responses, rather than in the development of the immune system.

The interaction of protein ligands and their receptors can be modified using a number of specific tools. For example, monoclonal antibodies (mAbs) which specifically recognize the ligand can be used to prevent or modify ligand/receptor binding, by virtue of recognition of the binding site, or by physically interfering with the interaction. Alternatively, anti-ligand mAbs can influence receptor signaling by influencing the binding of other ligands, when multiple ligands exist for a receptor. Such complicated effects have been noted for mAbs to the B7 family of CD28 ligands (Lenschow et al. J. Exp. Med. 181: 1145-1155 (1995)). Anti-ligand mAbs may have even more subtle effects in systems where multiple receptors exist for a particular ligand, eg. by modifying ligand binding to one receptor but leaving binding to another receptor unchanged. MAbs which recognize the receptor can also be used to modify ligand binding, or may themselves induce or modify receptor signaling. Thus anti-receptor mAbs can be antagonistic or agonistic. Examples of mAbs used in the mouse or human systems to modify ligand/receptor interactions of TNF/TNF-R family members include mAbs specific for TNF, for CD40L, for LT-β, for Fas-L, and for TR2/HVEM, among others. MAbs can be used to block the initiation or development of immunologic and other diseases. For example, anti-CD40L has been used in treatment of systemic lupus erythematosis (SLE), and to control organ transplant failure.

Potent inhibitors of ligand/receptor interaction can also be created by cloning the sequences which encode the extracellular portion of receptor sequences to sequences which encode human immunoglobulin (Ig) heavy chain, then expressing the hybrid gene, using an appropriate gene promoter, in an appropriate cell line. Purified receptor-Ig fusion proteins can be used in vitro and in vivo to bind to available protein ligand, and thus modify the interaction of the ligand with the native, cell bound, receptor. Modification can occur by a variety of mechanisms, similar to those outlined above for anti-ligand mAbs. Examples of receptor-Ig fusion proteins used in the mouse or human systems to modify ligand/receptor interactions of TNF/TNF-R family members include TNF-R55-Ig, TNF-R75-Ig, LTβ-R-Ig, and OX40-Ig, among others. Receptor-Ig fusion proteins can be used to block the initiation or development of immunologic and other diseases. For example, TNF-R75-Ig has been used to treat Inflammatory Bowel Disease (IBD).

Herein we demonstrate that a mAb which specifically binds to murine and human TWEAK blocks the development of a prototypical antigen-driven immunological disorder, Graft-Versus-Host Disease (GVHD). Our invention anticipates the use of TWEAK and TWEAK receptor(s) modifying reagents to treat a variety of immunological disorders which result from the introduction of foreign antigen into patients, such as GVHD which results from bone marrow or stem cell transplantation, and organ transplant failure resulting from graft rejection. Furthermore this invention anticipates the use of TWEAK and TWEAK receptor(s) modifying reagents to treat a variety of autoimmune disorders, such as SLE, Idiopathic Thrombocytopenia Purpura, Wegener's Granulomatosis, Polyarteritis Nodosa, Retinal Uveitis, Rapidly Progressive Crescentic Glomerulonephritis, Rheumatoid Arthritis, Multiple Sclerosis, and ulcerative colitis, among other examples. Other anticipated uses include treatment of acute and chronic inflammatory conditions, such as allergic inflammation, asthma, eosinophilia, Graves' disease, and Chagas' disease, among others.

Materials and Methods

Mice

Six to eight week old female mice of the DBA/2 and C57BI/6 strains, and the (DBA/2×C57BI/6)F1 cross were purchased from Jackson Laboratory (Bar Harbor, Me. USA), housed under conventional barrier protection, and handled in accordance with institutional guidelines.

Monoclonal Antibodies

Monoclonal antibodies which recognize human and murine TWEAK protein were generated in Armenian hamsters using soluble human TWEAK protein that had been generated in baculovirus and purified as described (Chicheportiche et al., J. Biol. Chem. 51: 32401-32410 (1997)). For the first immunization each hamster received 50 µgs TWEAK in complete Freund's adjuvant (CFA), injected ip. For the subsequent immunizations (days 14, 28, and 42 after the primary immunization) each hamster received 50 (days 14 and 28) or 33 (day 42) µgs TWEAK in Incomplete Freund's Adjuvant (IFA), ip. The final immunization before fusion of the spleen cell for hybridoma formation was with 100 µgs TWEAK without adjuvant, ip. Hybridoma generation was performed using standard procedures (Lerner, Yale J. Biol. Med. 54: 387-402 (1981)).

The hybridoma which produces anti-murine CD40L mAb MR1 (Noelle et al., Proc. Natl. Acad. Sci. USA 89: 6550-6554 (1992)) was purchased from ATCC (Rockville, Md. USA).

The hybridoma which produces anti-KLH mAb Ha4/8 was obtained from Dr. Mendrick (Human Genome Sciences, Inc. Rockville, Md. USA).

ELISA Analyses of mAb Activity

Anti-human TWEAK mAbs were tested for their ability to bind to human and murine TWEAK in a variety of experimental formats. Several mAbs raised against human TWEAK protein also recognized the mouse TWEAK protein in an initial screening of mAB activity which was done using ELISA format assays. Murine TWEAK protein was generated in baculovirus using methods similar to those described for human TWEAK protein (Chicheportiche et al., J. Biol. Chem. 51: 32401-32410 (1997)). Purified human and murine TWEAK proteins were coated onto 96 well plates, and various hamster mAbs were tested for their ability to bind to these immobilized proteins. The capture of hamster mAb by the immobilized TWEAK proteins was visualized using Peroxidase-coupled donkey anti-hamster IgG (Jackson ImmunoResearch, West Grove, Pa. USA), and an appropriate peroxidase-dependent enzymatic reaction.

FACS Analyses of mAb Activity

Soluble TWEAK protein induces apoptosis in HT29 cells, indicating that these cells express a TWEAK receptor (Chicheportiche et al., J. Biol. Chem. 51: 32401-32410 (1997)). Purified mAbs (10 µg/ml) were tested for their ability to block the binding of FLAG-tagged murine or human TWEAK to HT29 cells, as detected by a biotinylated anti-FLAG antibody, streptaviden-peroxidase, and appropriate enzymatic substrate.

Induction of Chronic GVHD 6-8 week old DBA/2 and B6D2F1 female mice were sacrificed, and the spleens were removed using sterile technique. Single cell suspensions were made by gently grinding the organs between rough glass slides, allowing gross debris to settle out, then pelleting the cleared supernatant. This cell pellet was resuspended in Gey's buffered hypertonic solution, and incubated on ice for 3' to lyse red blood cells. 5 ml Geys was used per each spleen disrupted. The cell solution was pelleted again, resuspended in sterile, pyrogen-free PBS, pelleted, and resuspended a second time in sterile, pyrogen-free PBS. Cell number was determined using a hemocytometer, and the cell density was adjusted to $2\times10^8$/ml. This solution was then passed through a sterile 70 um cell filter, and kept on ice until use, 6-8 week old B6D2F1 female mice were used as recipients. Each recipient was injected with 500 µl ($1\times10^8$) cells in the vail vein. Experimental groups received the DBA/2 graft (DBA/2>F1), while a set of control animals received a B6D2F1 graft (F1>F1). Animals were assayed for the development of chronic GVHD 14 days after injection.

Blocking Chronic GVHD

Mice received anti-TWEAK mAb AB.D3, anti-CD40L mAb MR1, control mAb Ha4/8, or no treatment. The treatment schedule was 250 µgs mAb ip 4 hours prior to graft injection, and 2, 4, and 6 days afterwards.

Assays of Disease Development

On day 14 of the experiment the mice were sacrificed and weighed. Then, the spleen was aseptically removed and weighed. The spleen index was calculated as the ratio of spleen to body weight for each animal in the control F1>F1 group, averaged to give a value of one. The average spleen index for all other groups is normalized to the control value. Splenocytes were then isolated from these spleens, as described above, then diluted to a concentration of $1\times10^7$ cells/ml in sterile PBS. For FACS analysis 100 µls of cell were stained for the following cell surface markers. All mAbs described were purchased from Pharmingen (San Diego, Calif. USA). The streptavidin reagent was purchased from Southern Biotechnology Corp (Birmingham, Ala., USA). Splenocytes were stained with biotinylated anti-H-2K$^b$ a haplotype marker which can distinguish the donor cells (H-2K$^b$−) from host cells (H-2K$^b$+) in various combinations with directly conjugated FITC or PE labelled anti-CD4, anti-CD8, anti-B220, anti-CD69, anti I-A$^d$, anti-L-selectin, and anti-H2D$^d$, in PBS/0.5% Bovine serum albumin (BSA)/0.1% sodium azide (FACS buffer) containing 10 µg/ml FcBlock™ (Pharmingen) to interrupt non-specific binding to Fc receptors. The cells were incubated with the mAbs for 1 h on ice. Each sample was then resuspended in 2 ml FACS buffer to wash, then centrifuged to pellet the cell. The cells were resuspended in FACS buffer containing CyChrome labelled streptavidin, which bound to the biotinylated mAb to provide a third channel for FACS analysis, washed a final time, and analyzed using FACscan instrumentation and Cellquest software (Becton Dickenson, San Jose, Calif. USA).

For in vitro analysis of Ig secretion cells were pelleted and resuspended in DMEM containing 10% Fetal Bovine Serum (FBS)/4 mM glutamine, at a concentration of 1×10$^7$ cells/ml. One ml per well was distributed into 6 well plates. Cell supernatants were recovered after 24 hours.

Source of Anti-TWEAK Antibodies

In one embodiment of this invention, antibodies (Abs) directed against TWEAK function as TWEAK blocking agents. Abs can be raised against monomeric, dimeric, or trimeric forms of the TWEAK protein, with or without heterologous subunits, if these exist. Furthermore, Abs can be raised against soluble, mutant, altered, or chimeric forms of TWEAK proteins. The anti-TWEAK Abs of this invention can be polyclonal or monoclonal (mAbs) and can be modified to optimize their ability to block TWEAK binding to its receptor(s), their in vivo bioavailability, stability, or other desired traits.

Polyclonal antibody sera directed against TWEAK are prepared using conventional techniques by injecting animals such as goats, rabbits, rats, hamsters or mice subcutaneously with human TWEAK in complete Freund's adjuvant (CFA), followed by booster intraperitoneal or subcutaneous injection in incomplete Freund's adjuvant (IFA). Polyclonal antisera containing the desired Abs directed against TWEAK are screened by conventional immunological procedures.

Hamster monoclonal antibodies (mAbs) directed against human TWEAK are prepared using conventional methods by injecting armenian hamsters subcutaneously with recombinant soluble human TWEAK in CFA, followed by booster intraperitoneal or subcutaneous injection in IFA. A hybridoma cell line (AB.D3.7.2) which produces the hamster anti-TWEAK mAb AB.D3 was deposited on Dec. 17, 1998 with the American Type Culture Collection (ATCC) (ATCC, University Boulevard, Manassas, Va. 20110-2209) according to the provisions of the Budapest Treaty, and was assigned the ATCC accession number HB-12622. All restrictions on the availability to the public of the above ATCC deposit will be irrevocably removed upon the granting of a patent on this application.

Various forms of anti-TWEAK Abs can also be made using standard recombinant DNA techniques (Winter and Milstein, Nature, 349, pp. 293-99 (1991)). For example, "chimeric" antibodies can be constructed in which the antigen binding domain from an animal antibody is linked to a human constant domain (e.g. Cabilly et al., U.S. Pat. No. 4,816,567; Morrison et al., Proc. Natl. Acad. Sci. U.S.A., 81, pp. 6851-55 (1984)). Chimeric Abs reduce the observed immunogenic responses elicited by animal Abs when used in human clinical treatments.

In addition, recombinant "humanized antibodies" which recognize TWEAK can be synthesized. Humanized Abs are chimeras comprising mostly human IgG sequences into which the regions responsible for specific antigen-binding have been inserted (e.g. WO 94/04679). Animals are immunized with the desired antigen, the corresponding Abs are isolated, and the portion of the variable region sequences responsible for specific antigen binding are removed. The animal-derived antigen binding regions are then cloned into the appropriate position of human antibody genes in which the antigen binding regions have been deleted. Humanized Abs minimize the use of heterologous (inter-species) sequences in human Abs, and are less likely to elicit immune responses in the treated subject.

Construction of different classes of recombinant anti-TWEAK Abs can also be accomplished by making chimeric or humanized Abs comprising the anti-TWEAK variable domains and human constant domains (CH1, CH2, CH3) isolated from different classes of immunoglobulins. For example, anti-TWEAK IgM Abs with increased antigen binding site valencies can be recombinantly produced by cloning the antigen binding site into vectors carrying the human IgM heavy chain constant regions (Arulanandam et al., J. Exp. Med., 177, pp. 1439-50 (1993); Lane et al., Eur. J. Immunol., 22, pp. 2573-78 (1993); Traunecker et al., Nature, 339, pp. 68-70 (1989)).

In addition, standard recombinant DNA techniques can be used to alter the binding affinities of recombinant Abs with their antigens by altering amino acid residues in the vicinity of the antigen binding sites. The antigen binding affinity of a humanized Ab can be increased by mutagenesis based on molecular modeling (Queen et al., Proc. Natl. Acad. Sci. U.S.A., 86, pp. 10029-33 (1989); WO 94/04679).

It may be desirable to increase or to decrease the affinity of anti-TWEAK Abs for TWEAK depending on the targeted tissue type or the particular treatment schedule envisioned. For example, it may be advantageous to treat a patient with constant levels of anti-TWEAK Abs with reduced ability to modify the TWEAK pathway for semi-prophylactic treatments. Likewise, anti-TWEAK Abs with increased affinity for TWEAK may be advantageous for short-term treatments.

The production of hamster anti-human TWEAK monoclonal antibody is illustrated in EXAMPLE 1.

Use of Anti-TWEAK mAb to Block the Development of Chronic GVHD, an Antigen-Driven Immunological Disease.

We now show the effects of a TWEAK blocking agent, mAb AB.D3, on the development of an immunological response in a mouse model of chronic graft-versus-host disease (GVHD). The ability to block chronic GVHD includes effects on B cell activation and proliferation, and on the generation of secreted IgG. Mice were treated intraperitoneally (ip) with 250 µgs anti-TWEAK mAb AB.D3, anti-KLH control mAb Ha4/8, anti-CD40L mAb MR1, or were left untreated. 4 hours later mice received 1×10$^8$ splenocytes isolated from DBA/2 mice, in an 0.5 ml injection given intravenously (iv). The iv injected DBA/2 splenocytes constituted the allograft. 2, 4, and 6 days after the graft was given, the mice were again treated with 250 µgs anti-TWEAK mAb AB.D3, anti-KLH control mAb Ha4/8, or anti-CD40L mAb MR1. A control group of mice received 1×10$^8$ B6D2F1 splenocytes, which cannot induce disease in B6D2F1 recipients. Alternatively, ungrafted and untreated B6D2F1 mice were used as controls. 14 days after the graft was given the mice were sacrificed and examined for evidence of disease.

Untreated graft-recipient mice manifest a variety of symptoms that are indicative of the development of chronic GVHD. Splenomegaly, or enlargement of the spleen, is evidence that donor T cells and host B cells have become activated, and are undergoing polyclonal expansion, with dramatic increases in cell number. The appearance of cell surface proteins such as CD69 on a subset of B cells is indicative of B cell activation. The loss of L-selectin molecules from CD4+ and CD8+ T cells is evidence of T cell activation. The secretion of Ig molecules, such as IgG classes, IgA, and IgE, either into the serum, or in in vitro cell culture assays, indicates that B cells have become activated, and have switched their Ig class. In this regard the appearance of anti-self Igs in the serum or in in vitro cell culture assays shows that Igs that are being produced have inappropriate autoantigen recognition. Finally, survivorship can be measured as an outcome of different treatment regimens.

We compared control mice to untreated allograft-recipient mice to examine the extent of splenomegaly, B cell activation, and Ig secretion during GVHD. Anti-CD40L mAb MR1 was used as a positive control in these experiments, since it has been previously shown that blocking the CD40L/CD40 interaction is an effective means of interfering with the development of chronic GVHD (Dune, et al., J. Clin. Invest, 94: 1333-1338 (1994)). A hamster mAb, Ha4/8, raised to Keyhole Limpet Hemocyanin (KLH) served as a negative control treatment. Results from 2 experiments are shown in Table 2. In both experiments treatment with anti-TWEAK mAb AB.D3 reduced the amount of splenomegaly (compared to untreated allograft-recipients) approximately 33%. Treatment with the negative control mAb Ha4/8 had no effect, while treatment with anti-CD40L mAb MR1 blocked splenomegaly by nearly 70%. To investigate cell populations affected by treatment with anti-TWEAK mAb AB.D3 FACS analyses were performed on splenocytes taken from the recipient mice 14 days after graft injection. Spleen cells from 3-4 mice per group were isolated and pooled. Activation of recipient B cells is a defining feature of chronic GVHD. In untreated and control mAb treated mice a small but readily visible proportion of the B200+ B cells express the activation marker CD69 (FIG. 4 and Table 3). In contrast, virtually no B200+ B cells in MR1 or AD.B3 treated mice express CD69. Lack of measurable B cell activation in the spleen of AB.D3 mice could be due to one or more of several mechanisms of action, including failure of T cell activation, failure of B cell activation, or cell death (apoptosis). Next we measured total IgG in cultures of splenocytes in mice from different treatment groups to determine if the loss of the CD69 activation marker from the B cell populations correlated with a functional readout, i.e. IgG production. Untreated control mice, MR1 treated mice, and AB.D3 treated mice produced dramatically lower amounts of total IgGs than did untreated or Ha4/8-treated allograft-recipient mice (Table 4). This result shows that Ig secretion by activated B cells, a defining feature of chronic GVHD, is blocked by treatment with anti-TWEAK mAb. The use of anti-TWEAK mAb to block the development of chronic GVHD is illustrated in Example 2.

Other Antibody Mediated Diseases

Many organ-specific and systemic autoimmune diseases involve pathological antibody responses. Such conditions include: Myasthenia Gravis, autoimmune hemolytic anemia, Chaga's disease, Grave's disease, idiopathic thrombocytopenia purpura (ITP) Systemic Lupus Erythematosus (SLE), Wegener's Granulomatosis, Poly-arteritis Nodosa and Rapidly Progressive Crescentic Glomerulonephritis (From Benjamini, et al. Immunology, A Short Course, (Wiley-Liss, New York 3d ed. (1996)).

Although the etiology of SLE is undefined, a fair amount is known about the immunologic mechanism responsible for the pathology observed. For unknown reasons, patients with SLE produce antibodies against nuclear components of the body (antinuclear antibodies (ANA) notably against native double stranded DNA. Clinically the presence of these antibodies correlates best with the renal pathology that develops in SLE. These antibodies complex with DNA apparently derived from the breakdown of normal tissue, and as in any immune-aggregate disease, such complexes form deposits trapped against the basement membrane of the glomeruli, in arteriolar walls and in joint synovial spaces. These complexes activate the complement cascade and attract granulocytes. The subsequent inflammatory reaction is characterized as glomerulonephritis, with resulting damage to the kidneys leading to proteinuria and hematuria.

SLE has been studied in murine models for decades. The development of SLE can be blocked using reagents such as CTLA4-Ig fusion protein and anti-CD40L, which interrupt critical steps in T and B cell activation (Grewal and Flavell, Immunol. Rev. 153: 85-106 (1996)). Recently, the therapeutic efficacy of a reagent specific for the murine CD40 ligand was evaluated in several models (Mohan, et al., J. Immunol., 154, pp. 1470-1480 (1995)). The acceleration of lupus by the transfer of cells which induce the production of pathogenic antibodies in vivo was shown to be inhibited by administration of a monoclonal antibody which blocks CD40/CD40 ligand interactions. Moreover a brief treatment of lupus mice with anti-CD40 ligand antibody had a sustained beneficial effect on their spontaneous disease long after the antibody had been cleared from their systems. The experimentation indicated that pathogenic B cells could not produce antibody even 9 months after the therapy suggesting that there was a delay of the expansion of autoimmune memory B cells resulting in long-term therapeutic benefits. Moreover, anti CD40L treatment was able to halt or delay the progression of established SLE in a spontaneously occurring mouse model (Kalled, et al., J. Immunol. 160: 2158-2165 (1998)). As we have shown that reagents which modify TWEAK/TWEAK receptor(s) interaction in vivo inhibit B cell activation and Ig production, reagents of this invention will be useful for treating or preventing SLE.

The normal immune response to some pathogenic infectious agents elicits autoantibody responses that can become excessive and present a medical problem. One example is Chagas' disease, an inflammatory cardiomyopathy which develops in humans and experimental animals with chronic *Trypanosoma cruzi* (*T. cruzi*) infection. Recently, several studies have identified anti-self antibodies in the sera of Chagas' disease patients (Bach-Elias et al. Parasitol. Res. 84: 796-799 (1998)). Furthermore, induction of heart-specific autoimmune responses has recently received substantial experimental support as a possible mechanism involved in the pathogenesis of human Chagas' cardiomyopathy. A recent study (Tibbetts, et al., J. Immunol., 152, pp. 1493-1499 (1994)) determined that cardiac antigen-specific antibodies are produced in *T. Cruzi*-infected C57BI/6 mice with heart disease. Upon infection with the Brazil strain of *T. Cruzi*, C57BI/6 mice develop a cardiomyopathy that is histologically similar to that observed in chronically infected humans. Antisera from these mice react with three cardiac antigens while C57BI/6 mice infected with the Guayas strain of *T. Cruzi* which do not develop cardiomyopathy did not produce such antibodies. These data indicate that these antibodies are specific markers of cardiomyopathy. The ability of TWEAK modifying agents to block B cell activation and Ig production will be useful in blocking the cardiac damage that occurs in Chagas' disease patients.

Another example of cell destruction by autoantibodies generated as a consequence of certain infectious diseases or for other unknown reasons is idiopathic thrombocytopenia purpura (ITP). In this condition antibodies directed to platelets result in platelet destruction (by complement or phagocytic cells with Fc or C3b receptor) which may lead to bleeding. Therapeutics which will inhibit such antibody mediated autoimmune reactions in vivo such as the TWEAK modifying agents of this invention—which inhibit antibody generation—will be useful to treat or prevent these autoimmune diseases as well.

The normal immune response to some pathogenic infectious agents can also elicit hypersensitivity reactions that can become excessive and present themselves as a medical problem. The most prevalent example of type I hypersensitivity is allergic reaction. These are mediated by IgE antibodies which bind via their Fc portion to receptors on mast cells and basophils to trigger the release of pharmacologically active agents that mediate anaphylaxis, ITP and Goodpasture's syndrome are sometimes thought to be Type II reactions which occur when IgM or IgG antibodies bind to antigen on the cell surface and activate the complement cascade. Granulocytes are then attracted to the site of activation, and damage from the release of lytic enzymes from their granules results in the destruction of cells. Rheumatic arthritis is thought to result from a type III hypersensitivity reaction mediated by immune complexes of antigen (in this case rheumatoid factor, an IgM autoantibody) that binds to the Fc portion of normal IgG. These immune complexes participate in causing inflammation of joints and the damage characteristic of this disease. As these pathologies are mediated in part by antibodies, therapeutics which will inhibit the generation of antibody, such as the TWEAK modifying agents of this invention, will be useful for treating or preventing these diseases as well.

Additional examples of diseases which cause significant antibody-mediated damage to the patient include Graves' disease and acute hemolytic anemia. It is anticipated that TWEAK modifying agents will show efficacy in preventing or treating such diseases.

Inhibition of Cellular Immune Responses

We have demonstrated that administration of reagents which modify the activity of TWEAK protein in vivo block the development of an antibody-mediated (humoral) immune disorder, chronic GVHD. Other potent immune system modifiers which are capable of blocking the development of chronic GVHD include anti-CD40L and CTLA4-Ig fusion protein. These reagents block critical steps in T and B cell activation (Grewal and Flavell, Immunol. Rev, 153: 85-106 (1996)). Therefore, therapeutic manipulation of these other potent immune system pathways has not been limited to the humoral immune responses. For example anti-CD40L and CTLA4-Ig have been used separately and together to control organ transplant rejection in animal models (Kirk et al., Proc. Natl. Acad. Sci. USA. 94: 8789-8794 (1997)). Much of the immune response to transplanted organs is Th1 T cell mediated, and consists of a cytotoxic cellular immune response. Such cellular immune responses are responsible for cell mediated damage in a variety of other immune disorders such as autoimmune diseases such as inflammatory bowel disease, rheumatoid arthritis, multiple sclerosis, diabetes, ulcerative colitis, and Crohn's disease, as examples. Based on the ability to block the development of chronic GVHD, our invention anticipates the use of TWEAK or TWEAK-receptor modifying reagents in the therapeutic treatment of cellular immune disorders.

Treatments Using

TWEAK and TWEAK-Receptor Modifying Agents The compositions of this invention will be administered at an effective dose to treat the particular clinical condition addressed. Determination of a preferred pharmaceutical formulation and a therapeutically efficient dose regiment for a given application is well within the skill of the art taking into consideration, for example, the condition and weight of the patient, the extent of desired treatment and the tolerance of the patient for the treatment.

Doses of about 5 mg/kg of a TWEAK or TWEAK-Receptor modifying agent are expected to be suitable starting points for optimizing treatment doses.

Determination of a therapeutically effective dose can also be assessed by performing in vitro experiments that measure the concentration of the modifying agent required to coat target cells (TWEAK or TWEAK-Receptor-positive cells depending on the modifying agent) for suitable (therapeutic) time periods. The FACS and ELISA receptor-ligand binding assays described herein can be used to monitor the cell coating reaction. Based on the results of such in vitro binding assays, a range of suitable modifying agent concentrations can be selected to test in animals.

Administration of the soluble modifying agents of this invention, alone or in combination, including isolated and purified forms of anti-TWEAK and anti-TWEAK-R antibodies, receptor-Ig fusion proteins, other TWEAK and TWEAK-receptor modifying reagents including naturally occurring or chemically derived reagents, and their salts or pharmaceutically acceptable derivatives thereof, may be accomplished using any of the conventionally accepted modes of administration of agents which exhibit immunosuppressive activity.

The pharmaceutical compositions used in these therapies may also be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The TWEAK and TWEAK-receptor modifying agents of this invention may, for example, be placed into sterile, isotonic formulations with or without cofactors which stimulate uptake or stability. The formulation is preferably liquid, or may be lyophilized powder. For example, the TWEAK and TWEAK-receptor modifying agents of this invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773, 319; EP 58,481), copolymers of L-glutamic acid and ethyl-L-glutamate (Sidman et al. Biopolymers, 22, pp. 547-56 (1985)); poly(2-hydroxyethyl-methacrylate) or ethylene vinyl acetate (Langer et al., J. Biomed. Mater, Res., 15, pp. 167-277 (1981); Langer, Chem. Tech., 12, pp. 98-105 (1982)).

Advantages of Therapeutic Compositions Comprising TWEAK or TWEAK-Receptor Modifying Agents The TWEAK and TWEAK-receptor modifying agents of this invention are capable of inhibiting immune responses, as shown by the inhibition of B cell activation and Ig production in the chronic GVHD model. The ability to selectively inhibit such immune mediated responses will be useful for treating immune disorders including various autoimmune diseases, organ transplant rejection, and acute and chronic inflammatory conditions. Treatment of such pathologic immune disorders generally employs immunomodulatory and immunosuppressive agents which have pleiotropic effects on a wide variety of cell types and immunological responses. These non-specific immunosuppressive agents are generally required in high and often cytotoxic doses that cause adverse side effects. For example, three general immunosuppressive agents currently used include steroids, cyclophosphamide and azathioprine. Steroids are pleiotropic anti-inflammatory agents which suppress activated macrophages and inhibit the activity of antigen presenting cells in ways which reverse many pathologic T cell effects. Cyclophosphamide, an alkylating agent, mediates cell death by inhibiting DNA replication and repair. Azathioprine is an anti-proliferative agent which inhibits DNA synthesis. These non-specific immunosuppressive agents are generally required in high doses which increase their toxicity (e.g. nephro- and hepatotoxicity) and cause adverse side effects. They are thus unsuitable for long term therapies.

Thus, there is an unmet need for additional agents and therapies which overcome the problems caused by conventional treatments.

The following are examples which illustrate the anti-TWEAK mAb of this invention, the methods used in the characterization of the mAb, and the use of the mAb to block an antigen-driven immunological disorder. These examples should not be construed as limiting: the examples are included for purposes of illustration and the present invention is limited only by the claims.

EXAMPLES

Example 1

Production of a Monoclonal Antibody to TWEAK Protein

Monoclonal antibodies which recognizes human and murine TWEAK protein were generated in Armenian hamsters using soluble human TWEAK protein that had been generated in baculovirus as described (Chicheportiche et al., J. Biol. Chem. 51: 32401-32410 (1997)). For the first immunization each hamster received 50 μgs TWEAK in complete Freund's adjuvant (CFA), injected ip. For the subsequent immunizations (days 14, 28, and 42 after the primary immunization) each hamster received 50 (days 14 and 28) or 33 (day 42) μgs TWEAK in Incomplete Freund's Adjuvant (IFA), ip. The final immunization before fusion of the spleen cell for hybridoma formation was with 100 μgs TWEAK without adjuvant, ip. Hybridoma generation was performed using standard procedures (Lerner, Yale J. Biol. Med. 54: 387-402 (1981)).

Initial screening of mAb activity was done using ELISA format assays. Murine TWEAK protein was generated in baculovirus using methods similar to those described for human TWEAK protein (Chicheportiche et al., J. Biol. Chem. 51: 32401-32410 (1997)). Purified human and murine TWEAK proteins were coated onto 96 well plates, and various hamster mAbs were tested for their ability to bind to these immobilized proteins. The capture of hamster mAb by the immobilized TWEAK proteins was visualized using HRP-coupled donkey anti-hamster IgG (Jackson ImmunoResearch, West Grove, Pa. USA), and an appropriate enzymatic reaction. Eight out of 23 mAbs recognized both murine and human TWEAK proteins (Table 1).

TABLE 1

| CLONE | Human TWEAK ELISA | Murine TWEAK ELISA | Ligand Blocking FACS | FACS Binding to hTWEAK/293 | FACS Binding to mTWEAK/293 |
|---|---|---|---|---|---|
| AB.D3.7.2 | +++ | +++ | + | + | + |
| AA.DB5 | +++ | − | +/− | + | − |
| AC.H5.24 | +++ | +++ | − | nd | nd |
| AA.G9 | +++ | − | +/− | + | − |
| AB.H12.1 | +++ | +++ | − | − | − |
| BA.F5.35.2 * | +++ | +++ | + | + | − |
| BG.A12.5 * | ++ | +++ | + | + | − |
| BE.D5 | ++ | − | +/− | + | − |
| AF.D4 | ++ | − | + | + | − |
| AB.G11.1 * | +++ | +++ | + | + | + |
| BE.B3.6.1 * | ++ | − | − | + | − |
| AA.AC2.3.2 | +++ | − | +/− | nd | nd |
| BB.B12.1.31.3 | ++ | − | +/− | + | − |
| AA.DG7.14 * | +++ | +++ | + | + | + |
| BD.A3 | ++ | − | − | − | − |
| BC.B10.21 * | +++ | +++ | + | + | + |
| BG.E8 | +++ | − | +/− | + | − |
| AE.C10.4 * | +++ | − | + | + | − |
| AA.BB4.2 * | +++ | − | + | + | − |
| AA.EC10.2 * | +++ | − | + | + | − |

TABLE 1-continued

| CLONE | Human TWEAK ELISA | Murine TWEAK ELISA | Ligand Blocking FACS | FACS Binding to hTWEAK/293 | FACS Binding to mTWEAK/293 |
|---|---|---|---|---|---|
| AD.B5.9 * | +++ | − | − | − | − |
| AB.D4.67.19 | +++ | − | − | − | − |

HUMAN TWEAK ELISA: mAbs were evaluated on their ability to bind to a human TWEAK coated plate.
MURINE TWEAK ELISA: mAbs were tested for their crossreactivity on a murine TWEAK coated plate.
LIGAND BLOCKING FACS: mAbs were tested as to whether they were able to block human TWEAK-flag binding to HT29 cells.
FACS ANALYSIS OF EBNA293 TRANSFECTANTS: Human and murine TWEAK cDNAs were used to transfect EBNA293 cells, and mAbs were tested for reactivity 3 days later The conservation of antigenic epitopes across species lines was unsurprising given the extent of protein homology seen between the murine and human forms of TWEAK (FIG. 1). FACS analyses were used to determine if anti-TWEAK mAbs could bind to TWEAK proteins expressed on the surface of a cell. Human and murine TWEAK cDNA sequences were cloned into the expression vector CH269 (Chicheportiche et al., J. Biol. Chem. 51: 32401-32410 (1997)), and these constructs were used in transfections to produce transient protein expression in EBNA 293 cells. Four mAbs, including AB.D3, bound well to EBNA293 cells expressing murine TWEAK (FIG. 2). These 4 mAbs were also capable of preventing the binding of human TWEAK to HT29 cells which are known to express one or more TWEAK-receptors (eg., FIG. 3), Together these FACS analyses indicated that anti-TWEAK mAbs specifically recognized TWEAK proteins, and were capable of modifying the ability of TWEAK proteins to bind to one or more TWEAK receptors.

Example 2

The Use of Anti-TWEAK mAb AB.D3 to Block the Development of Splenomegaly, Activated B Cells, and Ig Production in a Murine Model of Chronic GVHD Chronic GVHD was induced in 6-8 week old B6D2F1 female mice using DBN2 splenocyte grafts as described in methods. Each recipient was injected with 500 µl (1×10$^8$) cells in the tail vein. Experimental groups received the DBN2 graft (DBA/2>F1), while a set of control animals received a B6D2F1 graft (F1>F1 Mice received anti-TWEAK mAb AB.D3, anti-CD40L mAb MR1, control mAb Ha4/8, or no treatment, Animals were dosed with 250 µg mAb ip 4 hours prior to graft injection, and 2, 4, and 6 days afterwards. On day 14 of the experiment the mice were sacrificed and the spleen index was calculated as the ratio of spleen weight to body weight for each animal in the control F1>F1 group, averaged to give a value of one. The average spleen index for all other groups is normalized to the control value. The results from 2 independent experiments are shown in Table 2. Animals receiving the DBA/2 graft (DBA/2>F1), and left untreated or treated with control mAb Ha4/8 showed a dramatic increase in spleen weight when compared to F1>F1 graft controls. This result is reflected in the spleen index, which showed an increase from the normalized control value of 1.0 to 2.6. Treatment of mice with anti-CD40L mAb MR1 reduced the spleen index nearly to control levels (1.1), and treatment with anti-TWEAK mAb AB.D3 reduced splenomegaly by 35% to 1.7 (Table 2).

TABLE 2

| TREATMENT | EXPERIMENT 1 | EXPERIMENT 2 | AVERAGE |
|---|---|---|---|
| F1 > F1 (control) | 1.0 | 1.0 | 1.0 |
| DBA/2 > F1, untreated | 2.7 | 2.6 | 2.65 |
| DBA/2 > F1, Ha4/8 treated | 2.9 | 2.6 | 2.75 |
| DBA/2 > F1, MR1 treated | 1.1 | 1.1 | 1.1 |
| DBA/2 > F1, AB.D3 treated | 1.8 | 1.7 | 1.75 |

On day 14 of the experiment the mice were sacrificed and weighed. Then, the spleen was aseptically removed and weighed. The spleen index was calculated as the ratio of spleen to body weight for each animal in the control F1>F1 group, averaged to give a value of one. The average spleen index for all other groups is normalized to the control value.

FACS analyses were employed to analyze the activation state of lymphocyte populations in the spleens of control and diseased mice, representing the various treatment groups. Initially we analyzed the amount of donor cell engraftment in the various group of mice. Donor cells were detected in the spleens of host mice at approximately the same percentage (average=6.2%) in all DBA/2>F1 treatment groups (Table 3), This result indicated that the different mAb treatments were not affecting donor cell engraftment.

TABLE 3

| TREATMENT | % H-2K$^b$ negative (donor) cells |
|---|---|
| F1 > F1 (control) | 0.2 |
| DBA/2 > F1, untreated | 5.9 |
| DBA/2 > F1, Ha4/8 treated | 9.9 |
| DBA/2 > F1, MR1 treated | 5.5 |
| DBA/2 > F1, AB.D3 treated | 4.3 |

For FACS analysis splenocytes from each group of mice were stained on ice for 1 h with PE-coupled anti-H2k$^b$ and FITC-coupled anti-H-2D$^d$ to measure expression of MHC alleles. Host splenocytes are positive for both markers, but donor splenocytes are H-2k$^b$ negative. Percent values reflect events within the lymphocyte population, as determined by forward and side scatter characteristics.

Next, two markers of lymphocyte activation were employed: CD69 expression on B220+ B cells, and L-selectin expression of CD4+ and CD8+ T cells. When control and untreated DBA/2>F1 mice were compared we noted an increase in CD69+ B cells from 2.5% to 6.2% (Table 4). This increase in CD69+ B cell numbers was prevented by treatment with either MR1 (3.3%) or AB.D3 (2.1%) but not Ha4/8 (6.5%) (FIG. 4 and Table 3). Data from 2 experiments are shown in Table 4.

TABLE 4

| TREATMENT GROUP | % B220+/CD69+ (double positive) CELLS | | |
|---|---|---|---|
| | EXPERIMENT 1 | EXPERIMENT 2 | AVERAGE |
| F1 > F1, control | 2.5 | 2.0 | 2.25 |
| DBA/2 > F1, untreated | 6.2 | 5.5 | 5.9 |
| DBA/2 > F1, Ha4/8 treated | 6.5 | 4.7 | 5.6 |
| DBA/2 > F1, MR1 treated | 3.3 | nd | 3.3 |
| DBA/2 > F1. AB.D3 treated | 2.1 | 3.2 | 2.65 |

Splenocytes were stained with PE-labelled anti-3220 and FITC labelled anti-CD69 for 1 h on ice, washed with FACS buffer, then analyzed. Percentages are based events collected within the lymphocyte population, as determined by forward and side scatter characteristics.

For in vitro analysis of Ig secretion ELISA analysis was performed on splenocyte cell culture supernatants derived from spleens harvested from the various treatment groups. Results in Table 5 are from the second experiment, average of results from 3 mice per group. Treatment with MR1 or AB.D3 prevented the 4-fold increase in spontaneous IgG production observed in the untreated and Ha4/8 treated DBN2>F1 groups.

TABLE 5

| TREATMENT GROUP | SPONTANEOUS IN VITRO IgG PRODUCTION |
|---|---|
| F1 > F1, control | 125 ng/ml +/− 20 ng/ml |
| DBA/2 > F1, untreated | 750 ng/ml +/− 65 ng/ml |
| DBA/2 > F1, Ha4/8 treated | 500 ng/ml +/− 150 ng/ml |
| DBA/2 > F1, MR1 treated | 0 |
| DBA/2 > F1. AB.D3 treated | 125 ng/ml +/− 20 ng/ml |

For in vitro analysis of Ig secretion cells were pelleted and resuspended in DMEM containing 10% Fetal Bovine Serum (FBS)/4 mM glutamine, at a concentration of $1\times10^7$ cells/ml. One ml per well was distributed into 6 well plates. Cell supernatants were recovered after 24 hours. Values represent the average of 2 wells per mouse, with 3 mice represented for each treatment group.

---

The invention claimed is:

1. A method for blocking the development of or treating or reducing the severity or effects of kidney damage resulting from Systemic Lupus Erythematosus (SLE) in an animal, the method comprising the step of administering a therapeutically effective amount of an antibody to TWEAK (TNF-like weak inducer of apoptosis), wherein the antibody binds to a TWEAK polypeptide comprising the amino acids of SEQ ID NO:1 or SEQ ID NO:2.

2. The method of claim 1, wherein the animal is human.

3. The method of claim 1, wherein the antibody binds to a TWEAK polypeptide comprising the amino acids of SEQ ID NO:2.

4. The method of claim 1, wherein the antibody is a monoclonal antibody.

5. The method of claim 4, wherein the monoclonal antibody is the monoclonal antibody produced by the hybridoma having ATCC Accession No. HB-12622.

6. The method of claim 1, wherein the antibody is selected from the group consisting of a recombinant antibody, a humanized antibody, or a chimeric antibody.

7. The method of claim 1, wherein the antibody is an IgG.

8. The method of claim 6, wherein the antibody comprises a human constant domain.

9. The method of claim 6, wherein the antibody is a chimera of the antibody produced by the hybridoma having ATCC Accession No. HB-12622.

10. The method of claim 6, wherein the antibody comprises variable domains of the antibody produced by the hybridoma having ATCC Accession No. HB-12622.

11. The method of claim 1, wherein the antibody is administered by a parenteral, subcutaneous, or intravenous route.

12. The method of claim 1, wherein the antibody is administered as a liquid composition.

13. The method of claim 1, wherein the antibody blocks the binding of human TWEAK-Flag polypeptide to HT29 cells.

* * * * *